United States Patent [19]

Anderson et al.

[11] Patent Number: 4,808,700
[45] Date of Patent: Feb. 28, 1989

[54] IMMUNOGENIC CONJUGATES OF NON-TOXIC E. COLI LT-B ENTEROTOXIN SUBUNIT AND CAPSULAR POLYMERS

[75] Inventors: Porter W. Anderson, Rochester, N.Y.; John D. Clements, New Orleans, La.

[73] Assignee: Praxis Biologics, Inc., Rochester, N.Y.

[21] Appl. No.: 639,293

[22] Filed: Aug. 10, 1984

Related U.S. Application Data

[63] Continuation-in-part of Ser. No. 628,873, Jul. 9, 1984, abandoned, which is a continuation-in-part of Ser. No. 511,048, Jul. 5, 1983, Pat. No. 4,673,574, which is a continuation-in-part of Ser. No. 298,102, Aug. 31, 1981, abandoned.

[51] Int. Cl.$^4$ .................. C07K 17/00; C07K 15/00; A61K 39/02; C12Q 1/68; C12N 15/00; C12N 1/00; C12N 5/00
[52] U.S. Cl. ........................ 530/403; 530/807; 530/812; 530/808; 424/92; 435/6; 435/172.3; 435/320; 435/240.27; 935/12; 514/12
[58] Field of Search ............... 530/403, 807, 812; 424/92; 935/12; 514/12

[56] References Cited

U.S. PATENT DOCUMENTS

| | | | |
|---|---|---|---|
| 4,196,192 | 4/1980 | Kuo | 424/92 |
| 4,210,641 | 7/1980 | Brossard et al. | 424/180 |
| 4,220,717 | 9/1980 | Kuo | 435/101 |
| 4,237,224 | 12/1980 | Cohen et al. | 435/68 |
| 4,304,863 | 12/1981 | Collins et al. | 435/172 |
| 4,356,170 | 10/1982 | Jennings et al. | |
| 4,361,550 | 12/1982 | Kung et al. | |
| 4,404,279 | 9/1983 | Ricotti | |
| 4,411,888 | 10/1983 | Klipstein et al. | 424/92 |
| 4,427,653 | 1/1984 | Springer | |
| 4,451,446 | 5/1984 | Vandevelde | |
| 4,459,286 | 7/1984 | Hilleman et al. | |
| 4,496,538 | 1/1985 | Gordon | |

FOREIGN PATENT DOCUMENTS

| | | |
|---|---|---|
| 60129 | 8/1982 | European Pat. Off. |
| 95452 | 6/1983 | European Pat. Off. |
| 98581 | 1/1984 | European Pat. Off. |
| 125228 | 4/1984 | European Pat. Off. |
| 109688 | 5/1984 | European Pat. Off. |

OTHER PUBLICATIONS

Schneerson et al., New Developments with Human and Veterinary Vaccines, Alan R. Liss, Inc., New York, pp. 77–94, (1980).
Stein et al., J. Immunol., 128(3): 1350–1354, (1982).
Galanos et al., European J. Biochem., 8:332–36, (1969).
Zamenhof et al., J. Biol. Chem., 208:695–704, (1953).
Beuvery et al., Infect. Immun., 37(1):15–22, (1982).
Lin et al., Immunol., 46:333–42, (1982).
Schneersen et al., Progress in Allergy, Karger, Basel, vol. 33, pp. 144–158, (1983).
Anderson, Infect. Immun., 39(1):233–38, (1983).
Tsay et al., Abstract 3348, Federation Proceedings, vol. 42, No. 4, (Mar. 5, 1983).
Tsay et al., Abstract 217, Federation Proceedings, Abstract 43:1453, (1984).
Tsay et al., Infect. Immun., 45(1):217, (1984).
Finkelstein and Lospalluto, J. Exp. Med., 130:185, (1969).
Mekalanos et al., Nature, 306:551–557, (1983).
Bolivar and Backman, Methods in Enzymology, 68:245, (1979).

(List continued on next page.)

Primary Examiner—Alvin E. Tanenholtz
Attorney, Agent, or Firm—Pennie & Edmonds

[57] ABSTRACT

A conjugate, which is the reductive amination product of an immunogenic capsular polymer fragment, having a reducing end and derived from the capsular polymer of a bacterial pathogen, and the non-toxic polypeptide binding subunit of the heat-labile enterotoxin of Escherichia coli (LT-BNT). Also disclosed, are methods for the preparation of the conjugates and for the preparation of vaccines containing the conjugates which elicits an effective level of antibodies in humans. By administering an immunogenic amount of the conjugates, active immunization against systematic infection in young mammals caused by bacterial pathogens can be induced.

10 Claims, 3 Drawing Sheets

OTHER PUBLICATIONS

Chu et al., Infect. Immun., 40:245, (1983).
Clements and Finkelstein, Infect. Immun., 21:1036, (1978).
Finkelstein, Crit. Rev. Microbiol., 2:553, (1973).
Geyer et al., Med. Microbiol. Immunol., 165:271, (1979).
Gill et al., Infect. Immun., 33:677, (1981).
Klipstein and Engert, Infect. Immun., 23:592, (1979).
Klipstein and Engert, Infect. Immun., 31:144, (1981).
Klipstein et al., Infect. Immun., 32:1100, (1981).
Klipstein et al., J. Infect. Disease, 147:318, (1983).
Neill et al., Infect. Immun., 41:1056, (1983).
Ovary and Benaceraff, Proc. Soc. Exp. Biol. Med., 114:72, (1963).
Roberts and Lauer, Methods in Enzymology, 68:473, (1979).
Sack and Sack, Infect. Immun., 11:334, (1975).
Sanchez et al., FEMS Microbiol. Lett., 14:1, (1982).
Sansonetti et al., Infect. Immun., 34:75, (1981).
Schneerson et al., J. Exp. Med., 152:361, (1980).
Schwartz and Gray, Arch. Biochem. Biophys., 181:542, (1977).
Sheer et al., Gastroenterology, 65:895, (1973).
Shine and Dalgarno, Nature, 254:34, (1975).
Yamamoto et al., J. Bacteriol., 148:983, (1981).
Clements et al., 83rd Annual Meeting of the American Society for Microbiology, New Orleans, Mar. 6-11, Abstract No. B49, p. 31, (1983).
Dallas et al., J. Bacteriol., 139:850-858, (1979).
Jennings et al., J. Immunology, 127:1011-1018, (1981).
Mekalanos et al., Proc. Natl. Acad. Sci., U.S.A., 79:151-155, (1982).
Moselely et al., J. Bacteriol., 144:444-446, (1980).
Pearson et al., Proc. Natl. Acad. Sci., U.S.A., 79:2976-2980, (1982).
Uchida et al., Science, 115:901-903, (1972).

IMMUNOGENIC CONJUGATES OF NON-TOXIC E. COLI LT-B ENTEROTOXIN SUBUNIT AND CAPSULAR POLYMERS

CROSS-REFERENCE TO RELATED APPLICATIONS

This application is a continuation-in-part of copending U.S. application Ser. No. 628,873, filed July 9, 1984, now abandoned and a continuation-in-part of copending U.S. application Ser. No. 511,048, filed July 5, 1983, now U.S. Pat. No. 4,673,574 which is a continuation-in-part of application Ser. No. 298,102, filed Aug. 31, 1981, now abandoned, all of which are incorporated by reference herein.

1. FIELD OF THE INVENTION

This invention relates to the field of novel vaccine compositions, processes for producing them and methods for immunization of young warm-blooded animals, including human beings, against infections and disease caused by bacteria, including, for example, *Haemophilus influenzae* type b, *Escherichia coli, Neisseria meningitidis* serogroups A and C, *Streptococcus pneumoniae* serotypes 3, 6, 12, 14, 19, 23 and 51, and Pseudomonas.

This invention further relates to a process for the production of a non-toxic B subunit of the heat-labile enterotoxin (LT-B) from a human isolate of an enterotoxigenic strain of *Escherichia coli*. This process utilizes recombinant DNA techniques, in which the requisite gene sequence is inserted by means of a suitable DNA vector into a non-pathogenic microbial strain.

Methods are provided for the isolation and purification of the LT-B protein and for its use for immunological prophylaxis and therapy. Antiserum produced against the LT-B protein may be utilized for passive immunization against enterotoxin-induced diarrheal disease. Alternatively, such antiserum may be employed for the preparation of immunological diagnostic tests that are specific for the enterotoxins of *Escherichia coli* or of *Vibrio cholerae*.

2. BACKGROUND OF THE INVENTION

It is known that purified bacterial capsular polymers (CP) generally are immunogenic in mature humans and animals and can be used as vaccines against the corresponding systemic infections. As used in this application, the term "capsular polymers" refers to sugar-containing polymers, such as polymers of sugars, sugar acids, amino sugars, polyhydric alcohols and sugar phosphates, and does not refer to amino acid-containing polymers. These "capsular polymers" are frequently referred to in the medical literature as "capsular polysaccharides", though they may contain linkages other than glycosidic linkages and constituents other than sugars such as those listed above.

The capsular polymers of different bacteria vary widely in immunogenicity in the first year of human life. Some are moderately active, such as *Streptococcus pneumoniae* serotype 3 and *Neisseria meningitidis* serogroup A. The susceptibility to systemic infection by encapsulated bacteria is greater in the first year of life. The immunogenic response to many bacterial capsular polymers in children is age dependent, i.e., immunocompetence to CP increases to adult levels by about six years of age.

Among the inactive CP are those of *Haemophilus influenzae* type b, *Streptococcus pneumoniae* serotypes 6 and 12, and *Neisseria meningitidis* serogroup C. Examples of CP's which give an intermediate response in infants are *Streptococcus pneumoniae* serotypes 19 and 51.

2.1. INTACT CAPSULAR POLYMERS AS ANTIGENS IN VACCINES

Various investigators have isolated and purified intact capsular polymers which may be useful in or as vaccines. For example, U.S. Pat. No. 4,220,717 describes a process for the isolation and purification of immunologically active polyribosyl ribitol phosphate (PRP) from the capsular polymer of *H. influenzae* b. Additionally, U.S. Pat. No. 4,210,641 relates to polysaccharide extracts of *H. influenzae* having an apparent molecular weight greater than 200,000 daltons and composed principally of galactose, glucose and mannose and containing a small amount of osamines.

Several researchers have utilized these and other intact capsular polymers in formulations to achieve better immunological responses. For example, U.S. Pat. No. 4,196,192 discloses a vaccine containing purified intact PRP and whole *Bordetella pertussis* bacteria. This approach to increasing immunogenicity resulted in enhanced levels of anti-PRP and anti-pertussis antibodies in young mammals.

2.2. VACCINES CONTAINING CONJUGATES

Other researchers have studied conjugation of capsular polymers to carrier proteins in an effort to enhance antibody formation by the so-called "carrier effect". For example, Schneerson et al., Journal of Experimental Medicine 152: 361–376 (1980) describes *H. influenzae* b polymer-protein conjugates disclosed to confer immunity to invasive diseases caused by *H. influenzae* b. The reference documents the age-related immunological behavior of capsular polymers in infants and seeks to overcome this age-dependence by conjugation of the intact capsular polymer with a variety of proteins, including serum albumins, *Limulus polyphemus* hemocyanin and diphtheria toxin. The method of conjugation involves the use of a linking agent such as adipic dihydrazide.

Geyer et al., Med. Microbiol. Immunol. 165: 171–288 (1979), prepared conjugates of certain *Klebsiella pneumoniae* capsular polysaccharide fragments to a nitrophenyl-ethylamine linker by reductive amination, and the derivatized sugar was then attached to proteins using azo coupling.

2.3. USE OF CARRIER PROTEINS TO MAKE ANTISERUM TO HAPTENS

Carrier proteins can do more than enhance the immunogenicity of conjugated capsular polymers; they can also render haptens immunogenic. Haptens are defined as molecules that can bind specifically to an antibody or lymphocyte receptor but cannot induce an immune response (i.e. they are not immunogenic). To evoke an immune response, haptens must generally first be coupled to a larger molecule, or carrier, which is usually a heterologous protein. Injection of the hapten-carrier complex into an animal will then give rise to the production by B lymphocytes of antibodies, some of which will be capable of specifically binding to the free, uncoupled hapten molecule.

Among the earliest haptens to be studied were azo dye compounds such as aniline and o-aminobenzoic acid. Landsteiner and Lampl [Z. ImmunForsch. 26: 293 (1918)] coupled these compounds by diazotization to serum proteins. When injected with these artificially prepared azo-proteins, rabbits developed precipitating antibodies that were specific for the attached chemical moieties.

Other examples of haptenic compounds are dinitrophenol, which becomes immunogenic upon coupling as the dinitrophenyl (DNP) group to bovine serum albumin or to bovine gamma globulin (BGG), and lysergic acid diethylamide. Even formaldehyde has been shown to behave as a hapten; persons exposed to formaldehyde vapors from products or in laboratories have become "sensitized" to the compound, following the formylation of their endogenous macromolecules in vivo.

Haptenic behavior is not limited to small organic molecules, and polypeptide hormones up to the size of insulin are often poorly, if at all, immunogenic. To obtain high antibody titers to these hormones it is thus necessary to conjugate them to a carrier molecule (or to create larger molecules by crosslinking many of these polypeptides together).

The involvement of the carrier molecule is especially interesting in that the carrier plays more than a mere transport role. Ovary and Benaceraff [Proc. Soc. Exp. Biol. Med. 114: 72 (1963)] showed this by injecting rabbits with DNP-BGG. Injection of many immunogenic materials into animals will produce an immunological "memory" of the exposure. When a second injection is given later, there is thus a much more vigorous immune response. Indeed, when Ovary and Benaceraff injected DNP-BGG again, there was a strong, secondary response that led to markedly elevated levels of antibodies directed against both DNP and BGG. But when the second injection was instead made with DNP-egg albumin, a much weaker anti-DNP antibody response was noted. The difference in response was due to what has been called the carrier effect, and it appears to involve helper T lymphocytes.

Preliminary evidence indicates that all proteins may not be equally effective carrier proteins for a given hapten. Robbins, et al. (Infect. Immun. 40: 245–256) have presented data on experimental protein-polysaccharide conjugate vaccines in which the same polysaccharide hapten was conjugated to different protein carriers and the antibody response to the hapten was quantified. Significant differences were noted in the amount of anti-hapten antibody generated, indicating a major role for the carrier.

2.4.
ENTEROTOXIGENIC BACTERIA AND DIARRHEAL DISEASE

Acute diarrheal disease due to the temporary colonization of the small intestine by enterotoxigenic strains of certain bacteria is a major health problem of global significance. Among the responsible bacteria, perhaps the most widely recognized is *Vibrio cholerae*. Less well known but of greater practical significance are particular strains of *Escherichia coli* (*E. coli*) which, together with rotavirus, produce acute diarrheic episodes that are fatal each year to an estimated 10 million infants living in underdeveloped tropical countries [Black et al., Lancet i: 141 (1981)].

These *E. coli* strains also generally account for a high incidence of the acute diarrhea that afflicts visitors to tropical regions. Furthermore, they have a profound impact upon livestock as well, since Kohler [J. Am. Vet. Med. Assoc. 173: 588 (1978)] has reported that weanling animals, particularly calves, lambs and piglets, may be similarly affected.

Both *Vibrio cholerae* and the enterotoxigenic *E. coli* strains produce their diarrheic effects through production of an enterotoxin. The cholera enterotoxin has been isolated and purified to homogeneity by Finkelstein [Crit. Rev. Microbiol. 2: 553 (1973)]. Furthermore, Finkelstein and LoSpalluto [J. Exp. Med. 130: 185 (1969)] have separated a protein subunit from the cholera toxin that has reduced biological activity. What has emerged from these and from other studies is the finding that the cholera enterotoxin is an 84,000 dalton protein that consists of an A and a B subunit.

The A subunit (18,000 daltons) is responsible for the biological effects of the toxin but is incapable of binding to its target receptors alone. Through the action of sulfhydryl reagents, the A subunit may be cleaved into two polypeptide chains, with molecular sizes of 7,000 and 21,000 daltons. Of these chains only the larger, designated $A_1$, is active.

The B subunit, which has a size of 56,000 daltons, is essential for the expression of the activity of the A subunit. Apparently it acts by binding to a target cell and then facilitating penetration by the active A subunit. Finkelstein et al. [J. Immunol. 113: 145 (1974)] have shown that the B subunit consists of non-covalently associated subunits that can be dissociated by vigorous treatment with sodium dodecyl sulfate or at low pH with urea into five polypeptide chains.

The effects of cholera toxin have been demonstrated by Sheer et al. [Gastroenterology 65: 895 (1973)] in rabbit jejunum. In that system, the toxin causes a blood to lumen unidirectional flux of sodium. As a result, the intestinal fluid becomes low in protein, $Mg^{++}$ and $Ca^{++}$, and high in $K^+$, $Na^+$ and $HCO_3^-$, compared to normal serum levels. With these ionic changes, there is a concomitant outflowing of water to the lumen, for the maintenance of osmotic equilibrium with the blood plasma.

The precise structure of the cholera toxin receptor is unknown, but it appears to be a glycolipid. This observation is based upon a finding by King and van Heyningen [J. Infect. Dis. 131: 643 (1975)] that the binding of cholera toxin to membrane is inhibited by various glycosphingolipids. Of the compounds of this type examined, $G_{M1}$ (galactosyl-N-acetylgalactosaminyl(sialyl)-galactosylglucosylceramide) was most potent.

Once cholera toxin binding occurs, there is a stimulation of adenylate cyclase activity and a locking of that enzyme in the activated state. The result is an increase in intracellular levels of cAMP that in some way gives rise to the above ionic changes.

Enterotoxic strains of *E. coli* also mediate their diarrheic effects through the production of enterotoxins. These toxins are of two types, one of which is a relatively low molecular weight species of 2,000 daltons. Because it survives treatment at 100° C., this species is referred to as the heat-stable toxin (ST). A second toxin that is heat labile (LT) is remarkably similar to the cholera toxin.

As shown by Gill et al. [Infect. Immun. 33: 677 (1981)], E. coli LT consists of the same type and number of subunits as the cholera toxin, and the corresponding subunits have approximately the same molecular weights. As with cholera toxin, the B subunits of LT attach to intestinal mucosal glycolipid receptors, thus permitting penetration of the cell by the biologically active A subunit. The sequence of events from that point on is also similar. Most importantly, Clements and Finkelstein [Infect. Immun. 21: 1036 (1978)] have shown that E. coli LT is immunologically related to both the A and B subunits of cholera enterotoxin.

2.5.
IMMUNOLOGICAL APPROACHES TO THE PREVENTION AND CURE OF ENTEROTOXIGENIC DIARRHEAL DISEASE

The most practical means for combating the widespread morbidity and mortality caused by microbial toxin-induced diarrheal disease would be protective vaccination. In this case of the enterotoxigenic E. coli strains, three approaches might be taken.

First, somatic antigens could be used for immunization. Killed or attenuated bacteria could be employed for this purpose, but this approach entails some risk and is likely to be of limited effectiveness. If the cell killing or attenuation is incomplete, clinical disease may develop. Even if this does not occur, protection will be imperfect since antigenically dissimilar somatic serotypes will not be recognized.

Secondly, Acres et al. [Infect. Immun. 25: 121 (1979)] have shown that pilus-mediated anchorage is a prerequisite for the induction of diarrheal disease by certain strains of enterotoxin-secreting E. coli. Thus, interference with cellular adhesion would have a prophylactic effect. Such interference could be produced by vaccination with pilus antigens, but again any protection so conferred would be applicable only to antigenically similar bacteria. Morgan et al. [Infect. Immun. 22: 771 (1978)] have detected multiple antigenically dissimilar pilus antigens among animal and human enterotoxigenic E. coli strains.

Finally, it should be possible to vaccinate animals with the enterotoxin itself. The immunity thus established would provide protection against active challenge with any of the relevant E. coli strains that produce the toxin. For reasons not clearly understood, immunization with LT toxin appears to provide protection against strains producing both LT and ST. There would not be protection against strains that produce only ST, but these strains are in the minority. Klipstein and Engert [Infect. Immun. 23: 592 (1979)] have described the active immunization of rats with purified LT protein.

Although immunization may be achieved through the use of LT itself, the use of the biologically inactive B subunit (LT-B) alone should be almost as effective, and of course safer. The efficacy of this approach has been shown in rats by Klipstein and Engert [Infect. Immun. 31: 144 (1981)]. Such immunization should also confer protection against cholera-induced diarrheic attacks, because of the immunological relationship between LT and the cholera enterotoxin described above.

Klipstein et al. have also immunized rats with ST coupled to LT [Infect. Immun. 32: 1100 (1981)] or to the LT-B protein [J. Infect. Disease 147: 318 (1983)]. A patent based on such conjugates and their use as vaccines has been issued to Klipstein et al. [U.S. Pat. No. 4,411,888].

2.6.
RECOMBINANT DNA TECHNOLOGY

In current recombinant DNA procedures, specific DNA sequences are inserted into an appropriate DNA vehicle, or vector, to form recombinant DNA molecules that can replicate in host cells. Circular double-stranded DNA molecules called plasmids are frequently used as vectors, and the preparation of such recombinant DNA forms entails the use of restriction endonuclease enzymes that can cleave DNA at specific base sequence sites. Once cuts have been made by a restriction enzyme in a plasmid and in the segment of foreign DNA that is to be inserted, the two DNA molecules may be covalently linked by an enzyme known as a ligase. General methods for the preparation of such recombinant DNA molecules have been described by Cohen and Boyer in U.S. Pat. No. 4,237,224. Other useful general methods have been described by Collins and Hohn in U.S. Pat. No. 4,304,863. Because of their broad utility, these patents are hereby incorporated by reference.

Once prepared, recombinant DNA molecules can be used to produce the product specified by the inserted gene sequence only if a number of conditions are met. Foremost is the requirement that the recombinant molecule be compatible with, and thus capable of autonomous replication in, the host cell. Much recent work has utilized *Escherichia coli* (*E. coli*) as a host organism because it is compatible with a wide range of recombinant plasmids. Depending upon the vector/host cell system used, the recombinant DNA molecule is introduced into the host by transformation, transduction or transfection.

Detection of the presence of recombinant plasmids in host cells may be coveniently achieved through the use of plasmid marker activities, such as antibiotic resistance. Thus, a host bearing a plasmid coding for the production of an ampicillin-degrading enzyme could be selected from unaltered cells by growing the host in a medium containing ampicillin. Further advantage may be taken of antibiotic resistance markers where a plasmid codes for a second antibiotic-degrading activity, at a site where the selected restriction endonuclease makes its cut and the foreign gene sequence is inserted. Host cells containing properly recombinant plasmids will then be characterized by resistance to the first antibiotic but sensitivity to the second.

The mere insertion of a recombinant plasmid into a host cell and the isolation of the modified host will not in itself assure that significant amounts of the desired gene product will be produced. For this to occur, the foreign gene sequence must be fused in proper relationship to a signal region in the plasmid for DNA transcription called a promoter. Alternatively, the foreign DNA may carry with it its own promoter, as long as it is recognized by the host. Whatever its origin, the promoter is a DNA sequence that directs the binding of RNA polymerase and therefore "promotes" the transcription of DNA to messenger RNA (mRNA).

Given strong promotion that can provide large quantities of mRNA, the ultimate production of the desired gene product will be dependent upon the effectiveness of translation from mRNA to protein. This, in turn, is dependent upon the efficiency of ribosomal binding to the mRNA. In *E. coli*, the ribosome-binding site on mRNA includes an initiation codon (AUG) and an upstream Shine-Dalgarno (SD) sequence. This sequence, containing 3-9 nucleotides and located 3-11 nucleotides from the AUG codon, is complementary to the 3' end of *E. coli* 16S ribosomal RNA (rRNA) [Shine and Dalgarno, Nature 254: 34 (1975)]. Apparently, ribosomal binding to mRNA is facilitated by base pairing between the SD sequence in the mRNA and the sequence at the 16S rRNA 3' end. For a review on maximizing gene expression, see Roberts and Lauer, Methods in Enzymology 68: 473 (1979).

The introduction of LT plasmids from enterotoxigenic *E. coli* strains of human and porcine origin into other bacteria has recently been demonstrated by Neill et al. [Infect. Immun. 41: 1056 (1983)]. In that study, LT plasmids from *E. coli* were transferred by conjugation into *E. coli* K-12 strains and into strains of *Shigella flexneri, Shigella sonnei, Citrobacter freundii, Enterobacter cloacae, Klebsiella pneumoniae* and *Salmonella typhimurium.* Analysis of the transconjugants showed that in all cases the transferred plasmids were stably maintained in their hosts. LT gene expression measured by solid-phase radioimmunoassay varied widely, however, with maximal LT production occurring in *E. coli.*

Genetic engineering techniques can also be applied to produce the B subunit of LT. Dallas [European patent application Ser. No. 0060129] has described the cloning of the gene coding for LT-B from an *E. coli* isolate of porcine origin. The cistron encoding the B subunit of LT was cloned into vector pJJS500 by cleaving EWD299 with EcoRI and ligating this DNA to EcoRI cleaved pJJS500. The application stated that a plasmid specifying LT-B production without apparent LT-A contamination was thus obtained. It should be pointed out that no evidence was presented to support this claim, no mention was made of in vivo or in vitro studies, and there was no indication of successful antibody production, based on the gene product.

Yamamoto et al. [J. Bacteriol. 148: 983 (1981)] have described the cloning of the LT-B gene from a human *E. coli* isolate into plasmid pBR322. Some expression of the gene product was detected by growing the modified bacterium in a radiolabeled amino acid mixture and then analyzing crude cell lysates by SDS polyacrylamide gel electrophoresis. No effort was made, however, to purify or characterize the LT-B protein, and it is not known whether the level of gene expression was significant.

In other studies, Sanchez et al [FEMS Microbiol. Lett. 14: 1 (1982)] cloned the LT-B gene from a human isolate into vector pACYC184. Again, the gene product was neither purified nor characterized.

3.

SUMMARY OF THE INVENTION

The present invention relates to the covalent attachment of capsular polymer fragments derived from bacterial capsular polymers to bacterial toxins, toxoids or binding subunits by means of reductive amination. As used in the present application, the term "toxoid" means a form of a toxin wwhich has the antigenicity of the toxin without its toxicity.

The immunogenic conjugates of the invention are prepared by first forming reducing end groups on the sugars of the capsular polymers and reacting these with amine groups of the bacterial toxin, toxoid or binding subunit by reductive amination. The reducing end groups may be formed by any suitable method, including selective hydrolysis, e.g., by acids or enzymes, or by oxidative cleavage, e.g., periodate. The conjugation is preferably achieved by reductive amination in an aqueous solution containing cyanoborohydride anions.

The immunogenic conjugates of the invention may be formulated with a pharmaceutically acceptable carrier to produce a vaccine which elicits effective levels of anti-capsular antibody formations in young mammals, including human beings. The vaccine may be utilized to induce active immunization against systemic infection in young mammals caused by the respective encapsulated bacteria by administering an immunogenic amount of the conjugate to the mammal.

The immunogenic conjugates have been found to be less age dependent than the capsular polymers alone, and are useful for the active immunization of very young warm-blooded mammals against systemic infections by the respective encapsulated bacteria.

Furthermore, the immunogenic conjugates of the invention do not contain potentially toxic linking agents, such as adipic dihydrazide or p-nito-phenylethylamine, which have been used in conjugating carbohydrate to protein.

Finally, the immunogenic conjugates of the invention contain fragments of capsular polymers, not intact capsular polymers. The highly repetitive structure of capsular polymers may be in part responsible for their failure to expand the capacity for antibody production in infants. A conjugate of intact (highly polymerized) CP and protein may only partially overcome the immunologic disadvantages of CP alone.

On the other hand, the use of capsular polymer fragments on a carrier may circumvent the disadvantages of the repetitive structure. Additionally, the CP determinants of a conjugate having CP fragments are on the average closer to the carrier than are the CP determinants of conjugates having intact CP, and this proximity to carrier may be necessary for a more effective "carrier effect".

A further advantage lies in the use, for the protein carrier, of a bacterial toxin, toxoid or binding subunit against which children are routinely vaccinated, e.g., tetanus or diphtheria. Desired immunity to the protein carrier selected is induced along with immunity against the pathogens associated with the capsular polymer.

As described above, the role of the protein carrier of a protein-hapten conjugate vaccine in producing an optimal response to the hapten appears to be important. Since the initial step in antibody production involves binding of the antigen to antibody-producing cells, the use of a protein with high binding activity may optimize the antibody response to a conjugate vaccine. Bacterial toxins, and particularly the binding subunits of these proteins, have exceptional binding affinities for mammalian cells. The binding subunit of the heat-labile entertoxin of enteric bacteria (LT-B) is one of the best studied of these binding subunits. In accordance with the invention, these binding subunits are highly effective as carriers for haptens in conjugate vaccines.

Methods and compositions are also provided for the cloning and expression in single-cell host organisms of genes coding for the non-toxic subunit of the heat-labile enterotoxin (LT-B) of an enterotoxigenic E. coli strain. Also described are methods for the selection and culturing of the modified hosts to produce LT-B, and for the isolation and purification of this product.

The LT-B thus produced may be utilized by the methods of this invention for a number of important immunological processes. It may be formulated for the production of vaccines having utility in veterinary and human medicine. Through passive administration, the antibodies from such vaccines may be used for the prevention and/or treatment of cholera-like enterotoxins. As used in the present application, the term "chlolera-like enterotoxin" shall mean cholera toxin and LT, as well as immunologically related enterotoxins naturally produced by *E. coli, Vibrio cholera*, or other gram-negative enteric bacilli, or produced by expression of the gene encoding cholera toxin, LT or such related enterotoxin in any micro-organism, including strains of Salmonella, Yersinia, Pseudomonas, Shigella, Citrobacter, Klebsiella, and the like.

Unlike all other LT-B proteins that have been examined, whether derived from the chemical separation of the complete LT enterotoxin into its A and B subunits or from gene cloning, the product of this invention is non-toxic. This unusual freedom from toxic effects renders this invention uniquely suited for use in immunization procedures. To distinguish the LT-B of this invention from the toxic forms produced by other methods, it is designated LT-B non-toxic (LT-BNT).

4.

BRIEF DESCRIPTION OF THE FIGURES

The present invention may be more readily understood by reference to the following figures (not drawn to scale), wherein.

Figure 1:
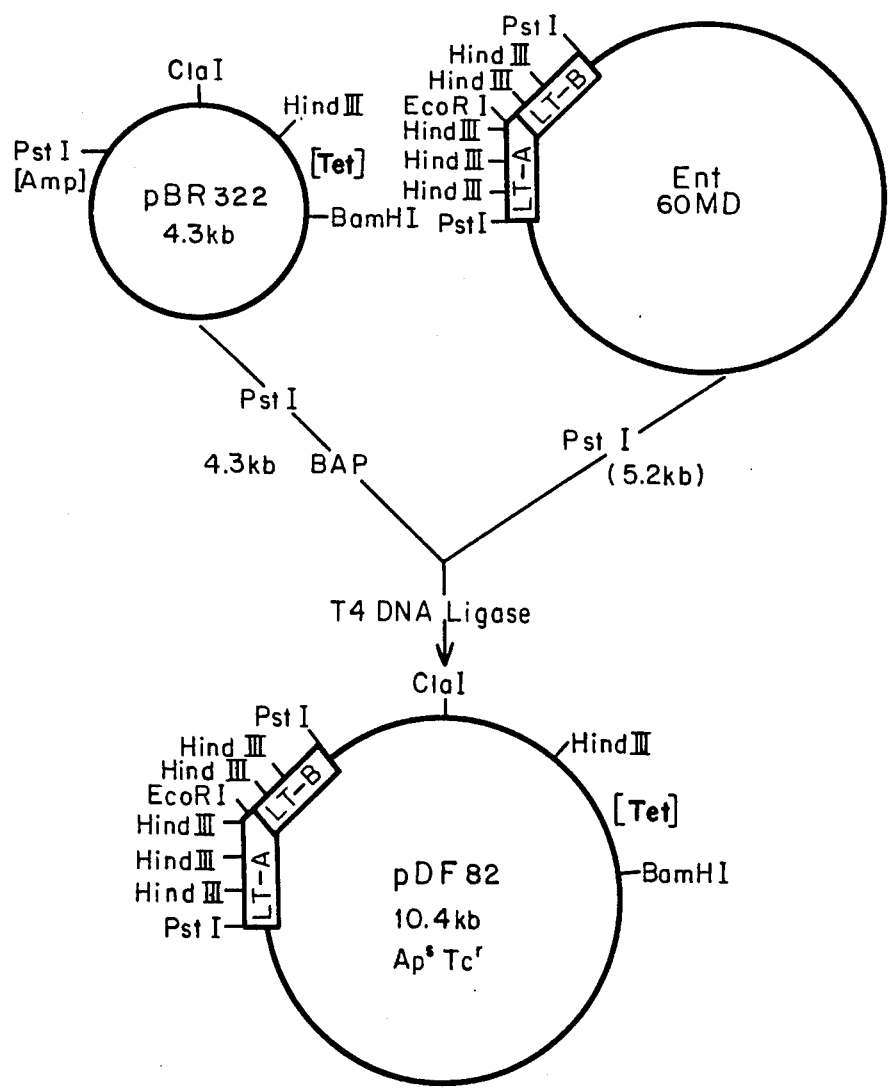
FIG. 1 is a schematic representation of the production of pDF82, an LT expression plasmid derived from pBR322, into which a 5.2 kb fragment containing the LT gene from an Ent plasmid of a human isolate of *E. coli* has been inserted.

5.

DETAILED DESCRIPTION OF THE INVENTION

The conjugates of the invention are formed by reacting reducing end groups of the capsular polymer fragment to primary amino groups of a bacterial toxin or toxoid to yield antigenic determinants of the capsular polymer covalently linked to the carrier protein. The reducing groups may be formed by selective hydrolysis or specific oxidative cleavage.

Antigenic fragments with at least one reducing end can be generated from capsular polymers by a variety of methods, depending upon the structural features of the particular capsular polymer. Limited oxidative cleavage by periodate (or related reagents) will leave aldehydic termini; such an approach will be limited to polymers having vicinal dihydroxy groups on a non-cyclic residue. Hydrolysis of a glycosidic linkage produces a reducing sugar terminus. Such hydrolysis can be most specifically accomplished enzymatically by glycosidases, but this application would be restricted to a relatively few capsular polymers, e.g., *Streptococcus pneumoniae* 8, for which glycosidases are known. Acidic hydrolysis is commonly used for hydrolysis of glycosidic linkages. The utility of this approach would be limited if the polymer contains acid-sensitive non-glycosidic linkages or if the polymer contains acid-sensitive branch linkages important to the antigenic specificity.

The conjugation is carried out according to the reductive amination process of Schwartz and Gray, Arch. Biochem. Biophys. 181: 542–549 (1977). Briefly, the process involves reacting the reducing capsular polymer fragment and bacterial toxin or toxoid in the presence of cyanoborohydride ions, or another reducing agent which will not reduce the reducing ends of interest nor adversely affect the toxin or toxoid capsular polymer. The cyanoborohydrate ions (or their equivalent) act solely as a mild selective reducing agent of the Schiff base intermediate formed between the carbonyl groups of the hydrolyzed capsular polymer fragment and amino groups of the protein. Thus, unlike previously employed conjugation procedures wherein the active molecules are joined by a linking agent which forms a part of the final product, the cyanoborohydride reducing anions utilized herein are not incorporated into the final product. This is important from the standpoint of controlling the potential toxicity of the final product. Evidence of covalent linkage is demonstrated by the fact that the association between, for exampled, a PRP moiety and the carrier protein persists despite salting-out of the protein in the presence of 8M urea, which has a great ability to disrupt non-covalent bonds.

Suitable carrier proteins are those which are safe for administration to young mammals and immunologically effective as carriers. Safety would include absence of primary toxicity and minimal risk of allergic complications. Diphtheria and tetanus toxoids fulfil these criteria; that is, suitably prepared, they are non-toxic and the incidence of allergic reactions is well documented. Though the risk of allergic reaction may be relatively significant for adults, it is minimal for infants.

In the "carrier effect" a weak antigen or hapten, by being attached to a stronger antigen as carrier (i.e., a heterologous protein), becomes more immunogenic than if it were presented alone. If an animal is previously immunized with the carrier alone, it may become "primed" for an enhanced response not only to the carrier antigen but also the attached weaker antigen. Infants are routinely immunized with tetanus and diphtheria toxoids. Thus, they would be primed for subsequent presentation of a capsular polymer antigen conjugated to either of these toxoids.

In general, any heterologous protein could serve as a carrier antigen. However, certain bacterial toxins such as tetanus and diphtheria may have an additional advantage in that they are composed of two portions, one of which (the "binding" subunit) has a strong affinity for binding to mammalian cell surfaces. Conceivably, conjugation to such a "binding" protein would permit the carried antigen to more effectively initiate responses in cells of the immune system.

The carrier proteins to which the capsular polymer is conjugated may be native toxin or detoxified toxin (toxoid). Also, by relatively recent mutational techniques, one may produce genetically altered proteins which are antigenically similar to the toxin yet non-toxic. These are called "cross reacting materials", or CRMs. CRM$_{197}$ is noteworthy since it has a single amino acid change from the native diphtheria toxin and is immunologically indistinguishable from it.

Conjugation of capsular polymer to native toxin may reduce toxicity, but significant toxicity may remain. Thus, further detoxification would be required. Conventional detoxification of protein toxins employs formalin, which reacts with free amino groups of the protein. Residual toxicity may still be a concern. Furthermore, spontaneous detoxification is possible with any particular lot of vaccine and remains an issue of concern with this approach.

Alternatively, native toxin may be detoxified with formalin to produce conventional toxoid before conjugation to capsular polymer. However, the prior formalin treatment reduces the number of free amino groups available for reaction with the reducing groups of the capsular polymer fragment. CRMs, thus, have significant advantages in that they have no inherent toxicity yet none of their amino groups are occupied by the formalin. A further advantage is that no biohazards exist in working with CRMs.

In the case of CRM$_{197}$, which is immunologically identical to native toxin, treatment with formalin (though there is not need to detoxify) greatly enhances the immunological response. It is thought that this is due to stabilization of the molecule against degradation by mechanisms of the body and/or aggregation by cross-linking (immunogenicity of particles increases with size).

For all of the above reasons, tetanus and diphtheria toxins are prime candidates for carrier proteins, yet there are others which may also be suitable. Though these others may not have the history of safety found with diphtheria and tetanus, there may be other overwhelming reasons to use them. For instance, they may be even more effective as carriers, or production economics may be significant. Other candidates for carriers include toxins of pseudomonas, staphylococcus, streptococcus, pertussis and *Escherichia coli*.

Suitable carrier media for formulating a vaccine include sodium phosphate-buffered saline (pH 7.4) or 0.125M aluminum phosphate gel suspended in sodium phosphate-buffered saline at pH 6 and other conventional media.

Generally, vaccines containing from about 5 to about 100 ug, preferably about 10 to 50 ug, are suitable to elicit effective levels of antibody against the capsular polymer in young warm-blooded mammals. Of course, the exact dosage would be determined by routine dose/response experimentation. Several small doses given sequentially would be expected to be superior to the same amount of conjugate given as a single injection.

The vaccines of the invention may be administered by injection to warm-blooded mammals of any age and is especially adapted to induce active immunization against systemic infections in young mammals caused by the pathogens *Haemophilus influenzae* type b, *Escherichia coli*, pneumococcus, meningococcus, streptococcus and pseudomonas.

This invention also relates to the use of gene splicing methodology to produce a completely non-toxic biologically inactive subunit of the enterotoxin of an enterotoxigenic bacterial strain. Following its purification, this LT-B subunit can be used as an immunogen for the production of polyvalent antiserum. Such antiserum has applicability to the prevention and cure in human beings or in other mammalian species of diarrheal disease that has as its origin enteric infection by strains of *E. coli*, *Vibrio cholerae* or other bacteria producing a cholera-like enterotoxin. The antiserum is also useful for the preparation of diagnostic tests for the presence of the cholera-like enterotoxins of these microorganisms. Alternatively, the LT-B subunit can be used as a carrier for the production of immunogenic conjugates.

For the purpose of illustration, the procedures of this invention are detailed using one particular enterotoxigenic stain of *E. coli* as an example. The fact that this microorganism was a human isolate may lead to a more potent antiserum for use in human beings. It must be emphasized, however, that there is strong cross reactivity between the comparable subunits of the toxins of many enterotoxigenic strains, whether they be of human, porcine or other origin. Thus this invention contemplates the potential use of any of them for this purpose, and the methods described herein are equally applicable to them all.

The methods of this invention entail a number of steps which, in logical sequence, include (1) identification and isolation of the gene encoding LT-B or a fragment thereof, (2) insertion of this gene or gene fragment into an appropriate cloning vehicle, (3) transfer of the genetically altered cloning vehicle into a compatible single-cell host organism, (4) selection and growth of properly modified hosts that can replicate and express the inserted gene sequences, (5) identification and purification of the gene product, (6) use of the gene product for antibody production, and (7) use of the specific antibodies for therapeutic, prophylactic and diagnostic purposes.

5.1

IDENTIFICATION AND ISOLATION OF LT GENES

The genes for the production of LT and its subunits are carried on plasmids (Ent plasmids) of enterotoxigenic *E. coli* strains. Thus a stool sample from a human being or other mammalian species afflicted with enterotoxin-induced diarrheic disease could serve as the crude source of the requisite gene sequences. Isolates from these sources may be grown in sufficient quantities using standard microbiological techniques that are well known to skilled practitioners in the art. Unfortunately, the ability to make enterotoxin confers no selective value upon the strains of *E. coli* that carry the Ent plasmid and produce enterotoxin. To monitor the transfer of the Ent plasmid into a stable laboratory strain such as *E. coli* K-12, a desirable first step, it is thus necessary to mark the plasmid in some way.

In the illustrative embodiment of the present invention, the plasmids of a human isolate of *E. coli* H10407 were phenotypically tagged by transposition from an F'tslac::Tn5 plasmid as described by Sansonetti et al. [Infect. Immun. 34:75 (1981)]. The tagged plasmids were then transferred by conjugation to K-12 strain 711, and an LT-producing transconjugant was selected. This transconjugant contained two large plasmids of a size ($6 \times 10^7$ daltons) that Gyles et al. [J. Infect. Dis. 130:40 (1974)] had shown to be characteristic of plasmids producing enterotoxin in H10407.

Verification of the fact that the transconjugant produced LT was made by enzyme linked immunosorbent assay (ELISA), using antibodies produced against LT, and by biologic activity as determined by induction of morphologic alterations in cultured mouse Y-1 adrenal cells. The plasmids thus transferred were isolated by the cleared lysate technique of Bolivar and Backman [Methods in Enzymology 68: 245–267 (1979)], and the specific LT gene sequences were isolated by restriction endonuclease cleavage.

In the illustrative embodiment, the purified ENT plasmid was cut with the restriction endonuclease Pst I, although any restriction enzyme or combination thereof could be employed so long as LT production (and subsequently LT-B production) is not destroyed by excision in the critical gene regions. The particular enzyme chosen would preferably be one that makes a single cut in the cloning vehicle used. Fulfillment of this second requirement may easily be achieved, since detailed restriction maps of many of the commonly used cloning vehicles are available.

Once appropriate cuts were made by Pst I in both the ENT plasmid and in the cloning vehicle, in this example plasmid pBR322, the LT gene fragment was ligated to the cloning vehicle by use of an appropriate ligating enzyme. Representative of ligating enzymes are the DNA ligases from E. coli and from bacteriophage T4. Such enzymes form new phosphodiester linkages in conjunction with ATP or $NAD^+$ as a cofactor.

Transformation of host bacterial cells with these recombinant DNA molecules containing the LT DNA fragments provides for the generation of copies of the requisite DNA, which can then be analyzed for production of LT as described above or used as a source of plasmid DNA for the subsequent isolation of specific gene fragments coding for production of LT-B only.

The insertion of the LT DNA restriction fragment into a cloning vector is easily accomplished when both the ENT plasmid and the described cloning vehicle have been cut with the same restriction enzyme, since complementary DNA termini are thereby produced. If this cannot be accomplished, it may be necessary to modify the cut ends that are produced by digesting back single-stranded DNA to produce blunt ends, or by achieving the same result by filing in the single-stranded termini with an appropriate DNA polymerase. In this way, blunt end ligation with an enzyme such as T4 ligase may be carried out. Alternatively, any site desired may be produced by ligating nucleotide sequences (linkers) onto the DNA termini. Such linkers may comprise specific oligonucleotide sequences that encode restriction site recognition sequences. The cleaved vector and the LT DNA fragment may also be modified by homopolymeric tailing, as described by Morrow [Methods in Enzymology 68: 3 (1979)].

Alternatives to the isolation of the LT gene, or fragments thereof, include but are not limited to the chemical synthesis of the gene sequences (if known) or the preparation of DNA that is complementary to the messenger DNA that encodes the LT gene.

5.2.

IDENTIFICATION AND ISOLATION OF LT-B GENES

The gene fragment that codes for production of LT-B is adjacent to and downstream from the gene fragment that codes for production of LT-A. There are a number of restriction endonuclease sites within the LT gene that flank these specific gene fragments. Thus, a restriction enzyme is chosen which does not cut into the structural gene for the fragment under study (LT-B).

Once identified and isolated, the LT-B gene or gene fragment is inserted into an appropriate expression vector, which contains the necessary elements for transcription and translation of the inserted gene sequences. Since the promoter region for the LT-B subunit is normally furnished by the A subunit gene and this toxic product is to be avoided, the expression vehicle must contain its own promoter which can be read in sequence with the LT-B gene. Many plasmids into which the LT-B gene may be inserted contain such promoter regions, the tetracycline resistance gene of plasmid pBR322 and the lac gene of plasmid pUC8 being only two examples.

The efficient transcription of the LT-B gene or gene fragment is further dependent upon the presence of specific initiation signals. One signal that is commonly employed is the ATG sequence. Sources of the ATG sequence include but are not limited to the cro or N genes of coliphage lambda and the *E. coli* tryptophan E, D, C, B or A genes. Such initiation sequences may be found among many other gene sequences into which the LT-B gene or fragment may be inserted, and they may be produced synthetically in the alternative.

Strong translation is tied to the availability of a Shine-Dalgarno (SD) sequence which facilitates efficient ribosomal attachment. Such SD sequences must be interposed between the promoter and the initiation signal, for efficient message readout. The objective high level production of the LT-B protein is thus dependent upon the insertion of the LT-B gene sequence downstream from promoter, SD and initiation sequences.

Numerous cloning vehicles meeting these requirements may be employed which include but are not limited to SV40, adenovirus, yeast, lambda gt-WES-lambda B Charon 4A and 28, lambda-gt-l-lambda B, M13-derived vectors such as pUC8, 9, 18 and 19, pBR313, 322 and 325, pAC105, pVA51, pACY177, pKH47, pACYC184, pUB110, pMB9, Co1E1, pSC101, pML21, RSF2124, pCR1 or RP4.

Many of these cloning vehicles contain one or more marker activities that may be used to select for desired transformants, such as ampicillin and tetracycline resistance in pBR322 and ampicillin resistance and $\beta$-galactosidase activity in pUC8. Selection is greatly simplified when the host cells into which such vectors are inserted contain none of these activities, and one of the activities is lost by virtue of the insertion of the LT-B gene or gene fragment.

The transfer of the recombinant cloning vector into the host cell may be carried out in a variety of ways. Depending upon the particular vector/host cell system chosen, such transfer may be effected by transformation, transduction or transfection.

Depending upon the quality and quantity of the LT-B subunit produced, one or more clones may have to be prepared. In the illustrative embodiment of this invention, it was necessary to transfer the LT-B gene successively into two plasmids pBR322 and finally into plasmid pUC8. This multiple cloning sequence was necessitated by the fact that while all clones produced LT-B protein, the pBR322 recombinants produced low levels of LT-B (c.a. 1 mg/liter) and yielded toxic gene products. This toxicity was manifested by analysis in the Y1 adrenal cell assay system, which is described in detail in Section 6.7.2., infra. The basis of this toxicity was not understood, although the toxic LT-A subunit was not detectable in the preparation.

In the specific embodiment described herein, final LT-BNT production at levels 50 fold higher than present in wild type enterotoxigenic *E. coli* strains was achieved.

5.3. PURIFICATION OF LT-BNT

As produced in *E. coli* K-12, LT-BNT remains in the periplasmic space. To free the desired subunit product of this invention it is thus necessary to disrupt the outer membrane. This is prefereably accomplished by sonication, or by other mechanically disruptive means, such as the French pressure cell.

Cell disruption could also be accomplished by chemical or enzymatic means. Since divalent cations are often required for cell membrane integrity, treatment with appropriate chelating agents such as EDTA or EGTA might prove sufficiently disruptive to facilitate the leakage of LT-BNT from the cells. Similarly, enzymes such as lysozyme have been used to achieve the same result with proteins other than LT-BNT. That enzyme hydrolyzes the peptidoglycan backbone of the cell wall. In the specific illustration of the invention described below, however, lysozyme caused a 60 percent loss of recoverable LT-BNT.

The application of osmotic shock could also be employed. Briefly, this could be accomplished by first placing the cells in a hypertonic solution which would cause them to lose water and shrink. Subsequent placement in a hypotonic "shock" solution would then lead to a rapid influx of water into the cells with an expulsion of the desired LT-BNT.

Once freed from the cells, LT-BNT may be concentrated by precipitation with salts such as sodium or ammonium sulfate, ultrafiltration or other methods well known to those skilled in the art. Further purification could be accomplished by conventional protein purification techniques including but not limited to gel filtration, ion-exchange chromatography, preparative discgel or curtain electrophoresis, isoelectric focusing, low temperature organic solvent fractionation, or countercurrent distribution. Purification is preferably carried out, however, by the exploitation of a peculiar property of LT, LT-B and LT-BNT—an affinity for binding to agarose.

Both the complete toxin and the B subunit bind tenaciously to the galaclosyl residues of agarose. Thus LT-BNT is best purified by the selective retention of the subunit following the passage of a solution containing LT-BNT through an agarose column. Once bound and purged of other proteins by washing the column with buffer, the subunit may be freed by passing a galactose-containing solution through the column. This affinity chromatographic technique works well with *E. coli* K-12 because it is a rough bacterial strain. Wild-type strains bind the LT-BNT produced to galactosyl residues in their outer membranes, and very little of the subunit can be recovered on agarose columns from these strains. Thus, while the technique has occasionally been successfully employed with wild-type strains, best results are obtained with *E. coli* K-12 into which the LT-BNT genes have been inserted.

5.4. PREPARATION AND USE OF ANTIBODIES AGAINST LT-BNT

One purpose of this invention is the production of the non-toxic subunit of the heat-labile enterotoxin of an enterotoxigenic *E. coli* bacterium, by recombinant DNA techniques. Such subunit may then be employed as an immunogen in a vaccine to produce a protective immunological response against bacterial-induced diarrheic infections in human beings or in animals. Because the LT-BNT subunit is antigenically related to the heat-labile enterotoxins of all of the enterotoxigenic *E. coli* strains and of *Vibrio cholerae*, such vaccination would provide wide immunity. The fact that the product of this invention is biologically inactive and completely non-toxic ensures that it can be used with a degree of safety that is unattainable with complete toxins or microorganisms, even if the latter are killed or attenuated.

After purification as described above in Section 5.3, the isolated LT-BNT subunit may be used directly as a vaccine or incorporated at an appropriate concentration into an adjuvant for vaccination. Such appropriate concentrations are known to one of skill in this field or determinable by routine experimentation.

Suitable adjuvants for the vaccination of animals include but are not limited to Freund's complete or incomplete adjuvant (not suitable for human or livestock use), Adjuvant 65 (containing peanut oil, mannide monooleate and aluminum monostearate), and mineral gels such as aluminum hydroxide, aluminum phosphate and alum; surfactants such as hexadecylamine, octadecylamine, lysolecithin, dimethyldioctadecylammonium bromide, $N_1$-N-dioctadecyl-N'-N-bis(2-hydroxyethyl-propanediamine), methoxyhexadecyl-glycerol, and pluronic polyols; polyanions such as pyran, dextran sulfate, poly IC, polyacrylic acid, carbopol; peptides such as muramyl dipeptide, dimethylglycine, tuftsin; and oil emulsions. LT-BNT could also be administered following incorporation into liposomes or other microcarriers, or after conjugation to polysaccharides, other proteins or other polymers.

The illustrative embodiment of this invention proved so immunogenic that high antibody titers were obtained in mice without the use of an adjuvant. [See section 6.11.1, infra.]

Through active immunization in this fashion, the protection of livestock, other domestic animals and human beings can be achieved. Such protection would depend primarily upon the production of an adequate secretary IgA response. For this reason, and because human and other mammalian neonates are relatively immunologically incompetent when most susceptible to diarrheic infection, it is preferable that a passive immunization approach be taken. Accordingly, anti-LT-BNT antiserum could be produced in a large mammalian species such as a goat, cow, steer, sheep, horse, or in avian species, and the IgG fraction isolated through plasmaphoresis or other means. This fraction could then be administered to human infants through a suitable carrier or infant food, such as infant formula or cereal. For livestock, the immune globulins could be given after incorporation into livestock feed or a suitable pharmaceutical vehicle. Livestock of particular interest are newborn piglets, calves and lambs.

The immune globulins of this invention can be combined with either a liquid or solid pharmaceutical carrier, and the compositions can be in the form of tablets, capsules, powders, granules, suspensions or solutions. The compositions can also contain suitable preservatives, coloring and flavoring agents, or agents that produce slow release. Potential carriers that can be used in the preparation of the pharmaceutical compositions of this invention include, but are not limited to, gelatin capsules, sugars, cellulose derivatives such as sodium carboxymethyl cellulose, gelatin, talc, magnesium stearate, vegetable oil such as peanut oil, etc., glycerin, sorbitol, agar and water. Carriers may also serve as a binder to facilitate tabletting of the compositions for convenient oral administration.

Of course, monoclonal antibodies could be produced through current technology to achieve the same result. Somatic cells with the ability to produce antibodies, such as B cells, may be fused with B-cell myeloma line cells to provide hybridoma cells. These cells may be cultured in vitro or as ascites tumors indefinitely to produce large quantities of specific antibodies. Because hybridoma cells may be readily cloned, it is possible to rapidly produce large numbers of cells, all of which produce the same specific antibody molecules directed to a common antigenic determinant. This exceptional uniformity in antibody production may be advantageous where the antibodies are to be used in specific diagnostic tests.

Lymph nodes and spleens of animals of animals primed by injection of an antigen are convenient sources of B cells, although it is equally feasible to remove these cells from unsensitized animals, and to prime them in vitro after isolation. Mouse and rat B lymphocytes are most frequently used in hybridoma production, but cells from rabbits, human beings, frogs or other animals might be used instead. In the preferred embodiment of this invention, mouse spleen cells sensitized to LT-BNT in vitro are used to make the fused cell hybrids.

Numerous specialized myeloma cell lines have been developed from lymphocytic tumors for use in hybridoma production [Kohler and Milstein, Europ. J. Immunol. 6: 511–519 (1976); Shulman et al., Nature 276: 269–270 (1978)]. Of the many such cell lines produced, P3/X63-Ag 8, P3/NSI/1-Ag 4-1, Sp2/0-Ag14, and S194/5.XX0.BU.1 have frequently been used. In the example of the present invention, a murine myeloma cell line designated X63-Ag 8.653 is preferred.

The fusion of antibody-producing spleen or lymph node cells with myeloma cells to produce hybridomas is usually carried out with an excess of splenocytes or lymphocytes over myeloma cells that may be as high as 20:1 although, typically, lower ratios are used. Fusion is facilitated by the use of a fusion-promoting agent such as UV-inactivated Sendai virus or polyethylene glycol (PEG). Gefter et al. [Somatic Cell Genet. 3: 231–236 (1977)] have reported that combining dimethyl sulfoxide with PEG further enhances cell fusion. Electrical devices are also available which can fuse cells with an exceptionally high degree of efficiency.

Once fusion has occurred, the hybridoma cells must be selected from the unfused parental cell strains. This selection process may be readily accomplished by culturing the cells in a medium that supports hybridoma but not parental cell growth. The somatic B cells used in the fusion have limited lifespans in culture and thus will be lost as they undergo sensecence and death, but the parental myeloma cells, with indefinite culture lifespans, must be eliminated by special selection techniques.

In the example of the present invention, myeloma cells lacking hypoxanthine phosphoribosyl transferase (HPRT$^-$) were used. These cells lack the scavenger pathway for the reutilization of hypoxanthine free base and cannot survive if an inhibitor, such as aminopterin, is used to block the de novo purine synthetic pathways. The myeloma parental cells may thus be selected against by culturing the fusion mixture in hypoxanthine/aminopterin/thymidine (HAT) medium, while the hybridoma cells will survive due to the contribution of HPRT by the antibody-producing fusion parental cells.

After a period of selection culturing, the surviving hybridoma cells may be cloned, stocks may be grown up by standard cell culture methods, and clones producing desired specific immunoglobulins may be detected by enzyme-linked immunosorbent assay (ELISA) or by other tests, based upon the use of the antigen against which the antibodies are directed.

The anti-LT-BNT antibodies obtainable through the use of this invention may further be used for the preparation of enterotoxin diagnostic tests. Such diagnostic systems could take the form of a radioimmunoassay, either in free solution or solid state. Alternatively, enzyme-linked immunosorbent assays could be produced as could assays based on immunoblot analysis. These assays could be direct or indirect, with the application of a second antibody directed against the anti-LT-BNT antibodies. Numerous enzymatic activities could be coupled to the antibodies, with peroxidase, glucose oxidase, $\beta$-glactosidase and alkaline phosphatase being only a few of the possibilities. Those skilled in the art will also recognize that there are numerous other ways in which anti-LT-BNT antiserum could be utilized in a diagnostic capacity, such as in one of a number of agglutination tests. In such agglutination assays, the interaction of antibodies and any cholera-like enterotoxigenic bacterial enterotoxins (or binding subunits therefrom) may be detected using systems in which the antibodies are coated onto particles coated with the anti-LT-BNT antibodies. Such particles may be latex beads, liposomes, erythrocytes, polyacrylamide beads, or any of a number of suitable polymers.

The following are non-limiting examples of methods for the preparation of exemplary immunogenic conjugates of the present invention and of LT-B, and their use in vaccines.

6.

EXAMPLES 6.1.

GENERATION OF LARGE, MEDIUM AND SMALL FRAGMENTS OF PRP CONTAINING REDUCING END GROUPS

The capsular polymer of *Hemophilus influenzae* type b is a linear polymer with the repeating unit [-3-$\beta$-D-ribosyl (1-1) ribitol (5-phosphate)-] (PRP). Generally, hydrolysis of PRP is carried out until the ratio of total to reducing ribose has dropped to 25 or below. The resulting mixture of size fragments may be fractionated by molecular sieve column chromatography to isolate the desired size range of fragments for conjugations. The method of obtaining fragments is as follows:

a. A sample of sodium PRP, (nucleic acid content 0.006%) containing 28.6 milligrams ribose was dissolved with distilled water to make a total volume of 9.2 ml in a 125-ml erlenmeyer flask and chilled in ice.
b. 1.02 ml of 0.1N $H_2SO_4$ was added.
c. Duplicate samples of 0.01 ml of the acidified PRP were transferred to test tubes held on ice (0-minute).
d. The flask was transferred to a boiling-water bath for 3 minutes, then chilled in an ice-water bath.
e. Step c was repeated (3-minute sample).
f. The samples were assayed for reducing power by the alkaline ferricyanide method standardized with D-ribose.
g. Based on the result (see Table 1), step d was repeated.
h. Step c was repeated (6-minute samples).
i. Step f was repeated.

TABLE 1

| Samples | Nanomoles of reducing ribose (av) | Ratio, total ribose/ reducing ribose |
|---|---|---|
| 0-min | 0.42 | 493 |
| 3-min | 6.08 | 34.0 |
| 6-min | 9.66 | 21.4 |

The result (see Table 1) indicated that, assuming the sole mode of hydrolysis had been at the (1-1) glycosidic linkage, the number-average chain length was 21.4 monomeric units, i.e., (ribitol-5-phosphate-3-ribose)

j. 0.102 ml 1N NaOH was added, and the pH was estimated by indicator paper (about pH 6).
k. The neutralized hydrolysate was lyophilized.
l. Bio-Gel P10 (Bio-Rad, Inc.) was equilibrated in 0.1M triethylammonium acetate and poured into a 1.5 cm diameter chromatographic column, giving a gel-bed height of 98 cm.
m. The lyophilized material (step k) was rehydrated with 2.7 ml water, and 0.3 ml of 1M triethylammonium acetate was added. This solution was applied to the column and elution was carried out with collection of 3.5 ml fractions.
n. The elution of ribosyl residues was determined by assay of 0.005-ml samples of each fraction for ribose content by the orcinol reaction with D-ribose as standard.
o. Fractions were combined into 3 pools, L, M, and S as indicated in Table 2, and the pools were assayed for total ribose and reducing ribose:

TABLE 2

| Pool | Fractions contained | Total ribose, micromoles | Ratio, total ribose/ reducing ribose | Est. Mn* | Range of Ve/Vo of fraction |
|---|---|---|---|---|---|
| L | 15–18 | 577 | 31.2 | 11,000 | ≦1.08 |
| M | 19–23 | 744 | 18.6 | 6800 | 1.09–1.38 |
| S | 24–34 | 1180 | 9.1 | 3400 | 1.39–1.99 |

*on the assumption that the sole hydrolysis was glycosidic.

p. The pools were lyophilized, re-hydrated with 10 ml water, re-lyophilized, re-hydrated with 1.5 ml water. 1.2 ml of the last solutions were transferred to microcentrifuge tubes and lyophilized in preparation for the conjugation reactions.

Conjugation of $CRM_{197}$ to Reducing Fragments of PRP a. To the microcentrifuge tubes containing lyophilized fragments, L, M, and S and an empty tube (C or control) were added potassium phosphate buffer pH 8, 2.7 milligrams $CRM_{197}$, and 4 milligrams sodium cyanoborohydride, such that the final volume was 0.2 ml and the phosphate buffer was at 0.2M.
b. The tubes were incubated at 37° C. with daily mixing.
c. After 18 days the tubes were centrifuged 2 minutes at 7000 G.
d. After determination that the majority of protein was in the precipitates, the precipitates were washed four times with ≦1 ml water.
e. The washed precipitates were made 8M in urea and warmed to 50° C., dialyzed against saline overnight at 4° C., and centrifuged. The supernates were separated and made 95% saturated in ammonium sulfate, held overnight at 4°, and centrifuged. The resulting precipitates were washed 3 times with 0.4 ml of 95% saturated ammonium sulfate, and suspended with 1 ml water. These colloidal suspensions were labeled $CRM_{197}$-PRP-L, -M, -S, and $CRM_{197}$-C, respectively.

The preparations were assayed for protein by means of the Folin phenol reaction with bovine albumin as standard and for ribosyl residues with the orcinol reaction with D-ribose as standard. The results are given in Table 4. The preparations were assayed for PRP antigenic activity by their ability (at concentrations of 50 micrograms protein/ml) to inhibit the binding of labeled native PRP to human anti-PRP antibody (Table 3).

TABLE 3

| Preparation Tested | % Antigen Bound | Antigenic Activity (ng PRP equivalence/ug protein) |
|---|---|---|
| none | 28.1 | — |
| native PRP, 0.5 ng/ml | 6.7 | — |
| native PRP, 5 ng/ml | 0.94 | — |
| $CRM_{197}$-C | 34.3 | 0.0 |
| $CRM_{197}$-PRP-S | 2.0 | 0.1 |
| $CRM_{197}$-PRP-M | 2.5 | 0.08 |
| $CRM_{197}$-PRP-L | 3.9 | 0.006 |

Thus, all the tested cojugates of $CRM_{197}$ with PRP fragments were antigenically active, while the control preparation in which $CRM_{197}$ was exposed to cyanoborohydride in the absence of PRP fragments was inactive as expected.

The preparations were assayed for immunogenicity in rabbits in comparison with high molecular weight purified PRP, and the results are given in Table 4. Rabbits given the PRP control or the $CRM_{197}$ -C control made barely detectable increases in anti-PRP antibody. Rabbits given any of the three $CRM_{197}$ -PRP conjugates made progressive increases after each injection; the titers after the third injection were 1000-fold greater than prior to immunization. In an experiment not illustrated a simple mixture of $CRM_{197}$ and PRP fragment preparation L was assayed in rabbits and found not to elicit anti-PRP antibody.

TABLE 4

ANTI-PRP ANTIBODY RESPONSE TO CONJUGATED AND CONTROL VACCINES OF WEANLING RABBITS PRIMED WITH ORDINARY DIPHTHERIA TOXOID*

| Rabbit Vaccine** | Pentose/ protein ratio | Anti-PRP Antibody, ng/ml, at age in weeks | | | |
|---|---|---|---|---|---|
| | | 7*** | 8*** | 9*** | 10 |
| 1 PRP (MW $10^5$) | | 10 | 12 | 28 | 40 |
| 2 PRP (MW $10^5$) | | 10 | 10 | 27 | 26 |
| 3 $CRM_{197}$-C (control) | — | 35 | 25 | 31 | 36 |
| 4 $CRM_{197}$-C (control) | | 16 | 34 | 40 | 48 |
| 5 $CRM_{197}$-PRP-S | 0.015 | 19 | 980 | 26,000 | 49,000 |

TABLE 4-continued
ANTI-PRP ANTIBODY RESPONSE TO CONJUGATED AND CONTROL VACCINES OF WEANLING RABBITS PRIMED WITH ORDINARY DIPHTHERIA TOXOID*

| Rabbit Vaccine** | Pentose/protein ratio | Anti-PRP Antibody, ng/ml, at age in weeks | | | |
|---|---|---|---|---|---|
| | | 7*** | 8*** | 9*** | 10 |
| 6 $CRM_{197}$-PRP-S | | 10 | 84 | 23,000 | 31,000 |
| 7 $CRM_{197}$-PRP-M | 0.0069 | 10 | 37 | 2,500 | 11,000 |
| 8 $CRM_{197}$-PRP-M | | 23 | 11,000 | 49,000 | 150,000 |
| 9 $CRM_{197}$-PRP-L | 0.0020 | 14 | 73 | 3,700 | 26,000 |
| 10 $CRM_{197}$-PRP-L | | 10 | 340 | 9,800 | 76,000 |

*The rabbits were New Zealand Whites obtained from Dutchland Farms immediately after weaning. At six weeks of age each was injected subcutaneously (s.c.) with 40 Lf of diphtheria toxoid (Massachusetts Dept. of Public Health) contained in 0.5 ml of 0.0125 M aluminum phosphate pH 6 (alum).
**The PRP vaccine was 30 ug PRP lot 17 contained in 0.1 ml saline. The other vaccines were 25 ug protein contained in 0.5 ml alumn.
***Injections of the indicated vaccine were given (s.c.) immediately after bleeding. There were two rabbits per vaccine. Listed are individual titers, determined by radio-antigen binding with $^3$H-labeled native PRP.

The protective potential of the anti-PRP antibodies induced by the conjugates was evaluated by testing the bactericidal activity of the rabbit sera of Table 4. The bactericidal titers were determined against *H. influenzae* b strain Eag by the methods of Anderson et al, Journal of Clinical Investigation, Volume 65, pages 885–891 (1980). Table 5 shows that before vaccination the sera were unable to kill the bacteria (reciprocal titers 2). After three injections the reciprocal titers of the rabbits receiving the $CRM_{197}$-PRP conjugates had risen to 16 or greater while titers of the rabbits receiving the CRM 197 control remained at 2.

TABLE 5
Bacterial Titers Against *H. influenzae* b Strain Eag of Sera of Weanling Rabbits Vaccinated With $CRM_{197}$ of Its Conjugates With Oligosaccharides S, M, and L of PRP*

| Rabbit | Vaccine given | Reciprocal serum dilution for 90% Killing | |
|---|---|---|---|
| | | Pre-vaccination | After 3 injections |
| 3 | $CRM_{197}$ control | 2 | 2 |
| 4 | $CRM_{197}$ control | 2 | 2 |
| 5 | $CRM_{197}$-PRP-S | 2 | 128 |
| 6 | $CRM_{197}$-PRP-S | 2 | 256 |
| 7 | $CRM_{197}$-PRP-M | 2 | 16 |
| 8 | $CRM_{197}$-PRP-M | 2 | 64 |
| 9 | $CRM_{197}$-PRP-L | 2 | 64 |
| 10 | $CRM_{197}$-PRP-L | 2 | 32 |

*Same vaccinations as described in Table 4.

6.2.
VARIATION OF PRP FRAGMENT RATIO TO $CRM_{197}$

In this example, the ratio of PRP fragment S to $CRM_{197}$ was varied and the conservation of antigenic activity of the $CRM_{197}$ component was examined in addition to the PRP component.

Preparation of $CRM_{197}$-PRP-S#2, A and B a. To microcentrifuge tubes A and B were added 0.15 ml each of the solution of fragments S described above, i.e., steps o and p. The solutions were lyophilized.
b. Tube A received 0.015 ml 2M potassium phosphate buffer pH 8, 0.1 ml of $CRM_{197}$ 5 mg/ml in 0.01M sodium phosphate buffer pH 7, and 0.015 ml of sodium cyanoborohydride 200 mg/ml.
c. Tube B received 0.002 ml of the pH 8 buffer and 0.1 ml of the $CRM_{197}$ solution. The resulting solution was lyophilized. The solids were suspended with 0.015 ml water, and 0.002 ml of the pH 8 buffer were added.
d. Tubes A and B were incubated at 37° C. for 13 days. To tube B an additional 0.002 ml of cyanoborohydride was added. Both tubes were incubated at 37° C. for an additional 3 days. (Note that due to the reduced reaction volume, the concentrations of reactants in B were higher than A.)
e. To A was added 0.06 ml water and 0.8 ml saturated ammonium sulfate (SAS). To B was added 0.175 ml water and 0.8 ml SAS.
f. The tubes were incubated 1 hour at 0° C. and centrifuged 20 minutes at 8000 G. The supernates were removed.
g. The precipitates were washed by suspension in 1 ml of 80% SAS, centrifugation at 8000 G 20 minutes, and removal of the supernates.
h. The precipitates were suspended with 0.1 ml water, and 0.4 ml SAS was added.
i. Same as step f.
j. Same as step g.
k. The precipitate in B was dissolved with 0.084 ml 9.5M urea (estimated final concentration 8M); 0.1 ml water and 0.8 ml SAS were added, and the precipitate was isolated as in step f. This precipitate was washed as in step g.
l. The precipitates in A and B were suspended with 0.2 ml water. The suspensions were separated into soluble (s) and insoluble (i) fractions by centrifugation 30 minutes at 8000 G, and the s fractions (supernates) were made 0.01M sodium phosphate buffer pH and reserved.
m. The i fractions (precipitates) were rendered more soluble as follows: they were made 8M in urea, which was then gradually removed by dialysis against 0.01M sodium phosphate buffer pH 7. The resulting solutions were recombined with the respective s fractions.
n. Preparations A and B were tested for protein content with the Folin phenol reagent and for PRP antigenic activity by the assay described above. Both had PRP activity; B exceeded A by about 13-fold, as shown below:

| Preparation | ng PRP equivalence/ug protein |
|---|---|
| $CRM_{197}$-PRP-S#2,A | 0.038 |
| $CRM_{197}$-PRP-S#2,B | 0.50 | o. Preparations A and B were tested for CRM antigenicity (activity as diphtheria toxoid (DT)) by inhibition of the binding of antibody to a sample of purified DT furnished by the Massachusetts Department of Public Health. Both had activity roughly equal to the DT on a weight basis; B exceeded A by about 4-fold, as shown below.

| Inhibitor tested | Antibody bound, $A_{400}$ | ug DT equivalence per ug protein |
|---|---|---|
| None | 2.43 | |
| DT, 0.5 ug/ml | 2.56 | |
| DT, 5 ug/ml | 1.93 | |
| DT, 50 ug/ml | 0.96 | |
| $CRM_{197}$-PRP-S#2,A,50 ug/ml | 1.25 | 0.52 |
| $CRM_{197}$-PRP-S#2,B 5 ug/ml | 1.67 | 2.0 | p. Preparations A and B were suspended in alum at 16 ug protein 1 ml, and three 0.5 ml injections were given to rabbits in the protocol described in Table 4 (except the animals were 8 weeks old at the onset and not primed by previous injections of diphtheria toxoid). The sera were tested for antibodies in the binding assay described in step o. Both A and B elicited antibodies to DT as well as to PRP, as shown in Table 6. Separate control experiments showed that similar rabbits housed in the same quarters did not display such increases in anti-DT antibody values in the absence of being injected with $CRM_{197}$ preparations.

TABLE 6

| Rabbit | Injected | Assay for antibody to | Antibody values at age | | | |
|---|---|---|---|---|---|---|
| | | | 8 wk | 9 wk | 10 wk | 11 wk |
| 5 | A | PRP, ng/ml | 47 | 60 | 210 | 13,500 |
| | | DT, $A_{400}$ | 0.136 | 0.168 | 1.28 | 3.81 |
| 6 | A | PRP | 21 | 25 | 19 | 420 |
| | | DT | 0.072 | 0.049 | 0.262 | 3.23 |
| 7 | A | PRP | 20 | 20 | 2000 | 10,500 |
| | | DT | 0.155 | 0.134 | 0.155 | 0.676 |
| 3 | B | PRP | 20 | 27 | 1600 | 4900 |
| | | DT | 0.075 | 0.061 | 0.227 | 2.45 |
| 8 | B | PRP | 23 | 20 | 2900 | 26,000 |
| | | DT | 0.065 | 0.023 | 0.231 | 2.07 |

6.3.

CONJUGATION OF VERY SMALL FRAGMENTS OF PRP TO DIPHTHERIA TOXIN, DIPHTHERIA TOXOID, $CRM_{197}$ AND LT-BNT

Generation of Very Small Fragments of PRP Containing Reducing End Groups a. A 12 ml solution of PRP lot 20 was made 0.1M in HCl at 0° C. and sealed in a glass flask (0 minute).
b. The flask was transferred to a boiling-water bath for 4 minutes, then chilled in an ice water bath.
c. A small amount of resulting white colloid was removed by extraction with ether and the resulting clear solution was lyophilized.
d. Bio-Gel P10 (Bio Rad, Inc.) was equilibrated in 0.01M ammonium acetate and poured into a 1.5 cm diameter chromatographic column, giving a gel bed height of 98 cm.
e. The lyophilized material was rehydrated with 1.5 ml water and neutralized with $NH_4OH$. This solution was applied to the column and the elution was carried out.
f. Fragments eluting at Ve/Vo range of 2.0-2.4 were collected and designated fraction vs.
g. Steps a-f were repeated to double the supply of fraction vs.
h. The combined vs fractions were lyophilized, rehydrated to yield 4 ml of a solution containing a total of 47 umoles of reducing sugar activity when assayed by the alkaline ferricyanide method standardized with D-ribose.

Preparation of Conjugates of PRP-vs Fragments to Native Diphtheria Toxin, Native Diphtheria Toxoid, $CRM_{197}$ and LT-BNT The following proteins are used as carriers in the present example:
(1) DTx—purified diphtheria toxin, lot 1, obtained from the Massachusettes Public Health Biologic Laboratories. Partial detoxification is accomplished by the linking to PRPvs. Residual toxicity is removed by formalin treatment in the presence of lysine by the method of Pappenheimer et al., Immunochemistry, 9: 891 (1972).
(2) DTd—conventional (formal) toxoid, lot DCP-27, also obtained from the Massachusettes laboratories.
(3) $CRM_{197}$—antigenically mutated version of the toxin protein, antigenically indistinguishable from toxin but non-toxic.
(4) LT-BNT—purified non-toxic binding subunit of the E. coli LT enterotoxin, prepared as described in Sections 6.7-6.10, infra.

The conjugation method is as follows:
a. Protein, potassium phosphate buffer (2M $KH_2PO_4$ titrated with 2M KOH to pH 8.0 at 25° C.) and PRPvs were combined in glass centrifuge tubes in the manner set out below.

| Solution | Protein | Buffer | PRPvs |
|---|---|---|---|
| (1) | 30 mg DTx | 240 umol P | 20 umol |
| (2) | 30 mg DTd | 240 umol P | 20 umol |
| (3) | $CRM_{197}$ | 80 umol P | 6.7 umol |
| (4) | 9 mg LT-BNT | 120 umol P | 11 μmol | b. Solutions (1)-(3) were lyophilized, and the lyophiles were dissolved with $NaCNBH_3$ solution, 2% w/v in water as tabulated below. Solution (4) was not lyophilized but was simply made up in the indicated volume with the components described. The pH of solution (4) was 8.0.

| Solution | 2% $NaCNBH_3$ |
|---|---|
| (1) | 1.2 ml |
| (2) | 1.2 ml |
| (3) | 1.4 ml |
| (4) | 0.5 ml | c. The tubes were incubated at 37° C.
d. After 14 days (18 days at 38° C. for the LT-BNT), four volume-equivalents of saturated ammnonium sulfate were added. These suspensions were held 3 hours at 0° C., then centrifuged 20 minutes at 9000 G.
e. The precipitates were washed twice each with 10 ml of neutral 70% saturated ammonium sulfate.
f. The washed precipitates were dissolved with a minimal volume of 9.5M urea and dialyzed against 0.067M sodium phosphate buffer, pH 7.8.

Formalin Treatment of the Conjugates a. The conjugates were further dialyzed against sodium phosphate buffer which also contained 0.025M lysine. (Small samples were reserved for toxicity testing prior to formalinization).
b. Formalin was added to a final concentration of 0.2% v/v.
c. After 17 days incubation (7 days for the LT-BNT) at about 24° C. the solutions were extensively dialyzed against the sodium phosphate buffer.
d. Centrifugation was performed to remove small amounts of insoluble material.

Processing to Achieve Final Container Products a. Antigen solutions (1)-(4) in isotonic sodium phosphate buffer were passed through 0.22-micron "Millex" filter units (Millipore Corp.) and injected into bottles containing sterile phosphate buffered saline.
b. The preparations were assayed for protein using the Lowry method.

c. Thimerosal was filtered and injected into the solution as 1/100 volume of a freshly made 1% w/v solution. Samples of 10 ml were taken for a sterility test. The bottles were attached to a manually operated sterile single use filling device (Multiple Additive Set, Travenol Laboratories). 2 ml glass vials were filled, stoppered, sealed, and immediately transferred to storage at 4° C.

Assays on Conjugate Preparations a. Phosphate content of the protein fraction

PRP is composed of the repeating unit ribosyl-ribitol-phosphate. Thus colorimetric assay of phosphate in the fraction precipitable by 5% trichloroacetic acid (TCA) is a sensitive index of the incorporation of PRP fragments into the protein.

Samples containing 100 mg protein were made 5% in TCA in a volume of 3 ml, held 20 minutes on ice, and centrifuged 15 minutes at 4° C. at 2000×g. The precipitates were washed with an additional 3 ml of 5% TCA, then with 5 ml ethanol. The washed precipitates were ashed to convert organic phosphate to inorganic phosphate (Pi), and the Pi was quantified by the method of Chen et al., Anal. Chem., 28: 1756 (1956). The results were as follows:

| Sample | nmol Pi/ug protein | Implied average no. of PRP repeating units/protein |
|---|---|---|
| (1) DTx-PRPvs | 0.11 | 6.8 |
| (2) DTd-PRPvs | 0.10 | 6.2 |
| (3) CRM$_{192}$-PRPvs | 0.10 | 6.2 |
| (4) LT-BNT-PRPvs | 0.033 | 0.40 | b. Electrophoretic Analysis

Samples of the conjugated antigens were analyzed by mercaptoethanol-sodium dodecyl sulphate-polyacrylamide gel electrophoresis (ME-SDS-PAGE) in the same gel alongside the respective starting carrier protein preparations.

DTd-PRPvs, like the DTd, displayed a disperse band at MW 61,000 daltons. In contrast, DTx-PRPvs and CRM$_{197}$-PRPvs differed greatly from the starting proteins. The protein of these two conjugates collected either at the beginning of or in the stacking gel (4% acrylamide) or at the beginning of the separating get (10% acrylamide). Thus, the conjugates appear to have been converted into macromolecular aggregates, presumably by cross-linking from the formalin treatment. DTd-PRPvs also contains some aggregated material. Electrophoretic analysis of LT-BNT-PRPvs showed that essentially all was in aggregated form.

c. PRP Antigen Equivalence per Unit Protein

The capacity of the conjugates to bind anti-PRP antibody was determined by the inhibition of the binding of labeled PRP by human anti-PRP antiserum, calibrated with PRP lot 19. (Because protein-bound polymer fragments cannot be assumed to bind to antibody in a weight-equivalent fashion to the high molecular weight polymer, quantitative chemical composition cannot be inferred from these data.)

| Sample | % Inhibition of $^3$H-PRP bound | ng PRP equivalence/ug protein |
|---|---|---|
| PBS control | (0) | — |
| PRP 19, 0.5 ug/ml | 6.7 | — |
| PRP 19, 5 ug/ml | 32 | — |
| PRP 19, 50 ng/ml | 90 | — |
| DTx-PRPvs, 5 ug protein/ml | 24 | 0.5 |
| DTd-PRPvs, 5 ug protein/ml | 48 | 2.2 |
| CRM$_{197}$-PRPvs, 5 µg protein/ml | 38 | 1.4 |
| LT-BNT PRPvs, 5 µg protein/ml | 19 | 0.33 | d. Diphtheria Toxoid Antigenic Equivalence Per Unit Protein

Retention of the capacity of the preparations to react with anti-DTd antibody was determined for all but the LT-BNT-PRPvs conjugate by inhibition of an enzyme-linked immunosorbent assay (ELISA) in which purified DTd is attached to the assay tube (solid phase). Inhibition of antibody binding to the attached DTd is calibrated by the same DTd used in the fluid phase.

| Sample | % Inhibition of Antibody Binding | ng DTd equivalence/ug protein |
|---|---|---|
| PBS control | (0) | — |
| DTd, 5 ug protein/ml | 24 | — |
| DTd, 50 ug protein/ml | 50 | — |
| DTx-PRPvs, 50 ug protein/ml | 46 | 0.68 |
| DTd-PRPvs, 50 ug protein/ml | 58 | 2.1 |
| CRM$_{197}$-PRPvs, 50 ug protein/ml | 26 | 0.11 | e. Diphtheria Toxic Activity

Samples of the original DTx and the conjugate DTx-PRPvs before and after formalin treatment were titrated for toxic activity by injection into the skin of a non-immune adult rabbit. DTx at doses of 0.002 ug and 0.02 ug produced the expected dermal lesions. DTx-PRPvs prior to formalin treatment produced dose-dependent lesions such that 0.2 ug was approximately equal to 0.002 ug DTx (100-fold reduction in toxicity by the conjugation). After formalin treatment, lesions were not generated by doses as high as 2 ug (at least 1000-fold reduction relative to DTx). Doses up to 2 ug of conjugates DTd-PRPvs and CRM$_{197}$-PRPvs were tested similarly and generated no lesions. The LT-BNT-PRPvs conjugate was not tested.

f. Induction of Anti-PRP Antibody Responses in Weanling Rabbits, Measured by Radioantigen binding The antigens were mixed with an aluminum phosphate adjuvant (0.0125M Al, pH 7) such that a 0.5 ml dose contained 25 ug protein. Two rabbits (for each antigen) were given three weekly injections beginning at age 7 weeks; the rabbits had been injected with DTd alone at age 5 weeks, for a hypothetical "carrier priming" effect. All the animals had anti-PRP rises in an anamnestic pattern, with titers of at least 10 ug/ml after the third vaccination. Antigens CRM$_{197}$-PRPvs, LT-BNT-PRPvs and DTd-PRPvs were also tested at 25 µg protein levels in pairs of rabbits that had not been "primed" with DTd. These rabbits produced strong anti-PRP responses similar to those in the "primed" rabbits with all of these antigens.

g. Induction of Anti-DTd Antibody Response in Weanling Rabbits, Measured by ELISA The anti-DTd antibody responses in the same "unprimed" rabbits (7–10) of the preceding subsection are as follows: Rises were roughly 10-fold after the second injection and another 2- to 5-fold after the third.

h. Sterility of the Sample Preparations

The samples were found to be sterile as determined using Fluid Thioglycollate (BBL cat. no. 11260, lot D4D LKL) as the growth medium.

6.4. USE OF PRP FRAGMENTS CONJUGATED TO DIPHTHERIA TOXOID AND CRM$_{197}$ AS VACCINES IN CHILDREN

Two groups of 8 children in the age range of 1 to 2 years old, (and specifically exempting children receiving routine vaccination with diphtheria toxoid protein at age 18 months) were given primary and secondary vaccinations as follows: Group I received injections of CRM$_{197}$-PRPvs, preparation as described in the preceding section, (25 ug protein in saline, subcutaneously); Group II received injections of DTd-PRPvs, preparation as described in the preceding section, (25 ug protein in saline, subcutaneously).

In the first visit, pre-vaccination blood specimens were taken; the child was vaccinated, then observed for 20 minutes for any sign of an anaphylactic reaction. In the second visit the procedure of the first visit was repeated. In the third visit, a post-secondary blood specimen was taken. Two of the children, one from each group, after consultation with the parents, were given a third vaccination to try to raise the antibody against PRP to protective levels. The interval between vaccinations was 1±½ month.

Group III consisted of children about 18 months old receiving a vaccine simultaneously with diphtheria toxoid protein in a separate site. This group contained 2 children; one received the CRM$_{197}$-PRPvs vaccine, the other received the DTd-PRPvs vaccine.

Symptoms were recorded for four successive days, with measurements of temperature, notation of behavioral indications of systemic illness and observations of inflammation at the injection site. These symptoms are summarized in Table 7.

TABLE 7
ADVERSE REACTIONS TO PRP-VS CONJUGATES TO CRM$_{197}$ AND FORMAL DIPHTHERIA TOXOID

| | | Injection | | |
|---|---|---|---|---|
| Vaccine | Symptom | Primary | Secondary | Tertiary |
| CRM$_{197}$-PRPvs | Fever | 1/8 | 0/8 | 0/1 |
| | Unusual behavior | 0/8 | 0/8 | 0/1 |
| | Local inflammation | 1/9* | 2/9 | 0/1 |
| | Local pain | 1/9* | 1/9 | 0/1 |
| DTd-PRPvs | Fever | 0/8 | 0/8 | 0/1 |
| | Unusual behavior | 0/8 | 0/8 | 0/1 |
| | Local inflammation | 1/9* | 0/9 | 0/1 |
| | Local pain | 1/9 | 1/9 | 0/1 |

*Includes one child who received diphtheria toxoid protein simultaneously in a separate site. No local symptoms were found. Systemic symptoms are not noted since these could not be distinguished from an effect of the diphtheria toxoid protein vaccine.

After CRM$_{197}$-PRPvs vaccination, one child had mild fever (99.8° C.) on the evening of primary vaccination; there was an instance of mild local inflammation once each after a primary, a secondary, and the one tertiary vaccination. After DTd-PRPvs there was an instance of local inflammation after one primary and one secondary vaccination. The administration of the vaccines was otherwise apparently free of adverse reactions.

Serum Antibody Responses

Antibodies to PRP as well as IgG antibodies to diphtheria toxoid were determined. After vaccination with CRM$_{197}$-PRPvs a consistent anti-PRP response pattern was seen. See Table 8. There was a distinct rise after the primary injection, usually an even larger rise after the secondary injection, and a large rise after the one tertiary. The final titers greatly exceeded those that have been produced by vaccination with PRP alone and greatly exceeded the accepted estimated protective minimal level of 0.15 ug/ml. The enhanced response was particularly evident in the four children under 18 months of age, where the response to PRP alone is generally inadequate for protection, and the geometric mean of the final titers in these four (8.4 ug/ml) is 175 times that found after vaccination of children 12–17 months old with PRP vaccine alone. The child receiving the primary vaccination simultaneously with diphtheria toxoid protein vaccine also had an excellent response.

IgG antibodies to diptheria toxoid increased in 6 of 8 children (as well as in the 9th, who also received diphtheria toxoid as part of the treatment). The antibody levels often increased so greatly that the dilution of post-vaccination serum used (1/1000) was insufficient to show the full extent of the rise.

After vaccination with DTd-PRPvs anti-PRP responses generally increased after both primary and secondary vaccination. (See Table 9). However, there were two children (12 and 14 month old) in whom no response was detected; and one child did not approach the protective level until given a third injection. The child receiving the primary vaccination simultaneously with diphtheria toxoid protein had an excellent response. Rises in IgG antibody to the diphtheria component were found in all children.

This example shows that injections of conjugates of the *H. influenzae* b capsular polymer fragment to diphtheria toxoid and CRM$_{197}$ is apparently harmless. CRM$_{197}$-PRPvs vaccination gave a clear indication of an enhancement of the anti-PRP response by the carrier effect—appreciated not only by the high titers but by the rises after secondary vaccination.

DTd-PRPvs had a less impressive enhancement. A likely explanation is that while CRM$_{197}$-PRPvs is a multimolecular aggregate, DTd-PRPvs is present mainly in unimolecular form similar to the original toxoid.

TABLE 8
ANTIBODY RESPONSE TO CRM$_{197}$-PRPvs

| Subject | Age at primary vaccination | Serum sample | Serum antibody, ug/ml | |
|---|---|---|---|---|
| | | | anti-PRP | IgG anti-DTd |
| 1 | 12 mo | pre-vac | 2.0 | 1.1 |
| | | post-1 | 4.5 | 10 |
| | | post-2 | 18 | 10 |
| 2 | 13 mo | pre-vac | 0.006 | 0.38 |
| | | post-1 | 0.040 | 1.7 |
| | | post-2 | 0.35 | 2.2 |
| | | post-3 | 4.8 | 1.9 |
| 3 | 14 mo | pre-vac | 0.020 | 4.5 |
| | | post-1 | 0.12 | 3.3 |
| | | post-2 | 2.0 | 4.3 |
| 4 | 16 mo | pre-vac | 0.025 | 0.06 |
| | | post-1 | 0.92 | 5.7 |
| | | post-2 | 29 | 9.1 |
| 5 | 27 mo | pre-vac | 0.025 | 3.0 |
| | | post-1 | 10 | 10 |
| | | post-2 | 58 | 10 |
| 6 | 29 mo | pre-vac | 0.13 | 6.1 |
| | | post-1 | 22 | 6.9 |
| | | post-2 | 180 | 7.4 |
| 7 | 30 mo | pre-vac | 2.2 | 6.5 |
| | | post-1 | 28 | 10 |

TABLE 8-continued
ANTIBODY RESPONSE TO CRM$_{197}$-PRPvs

| Subject | Age at primary vaccination | Serum sample | Serum antibody, ug/ml | |
|---|---|---|---|---|
| | | | anti-PRP | IgG anti-DTd |
| | | post-2 | 50 | 10 |
| 8 | 30 mo | pre-vac | 1.3 | 4.8 |
| | | post-1 | 6.5 | 10 |
| | | post-2 | 78 | 10 |
| 9 | 18 mo* | pre-vac | 0.34 | 3.1 |
| | | post-1 | 1.4 | 10 |
| | | post-2 | 8.2 | 10 |

*First injection of CRM$_{197}$-PRPvs given simultaneously with diphtheria toxoid protein vaccine in a separate site

TABLE 9
ANTIBODY RESPONSE TO DTd-PRPvs

| Subject | Age at primary vaccination | Serum sample | Serum antibody, ug/ml | |
|---|---|---|---|---|
| | | | anti-PRP | IgG anti-DTd |
| 1 | 12 mo | pre-vac | 0.020 | 0.060 |
| | | post-1 | 0.020 | 10 |
| | | post-2 | 0.020 | 10 |
| 2 | 12 o | vac | 0.055 | 0.03 |
| | | post-1 | 0.080 | 3.1 |
| | | post-2 | 1.8 | 10 |
| 3 | 13 mo | pre-vac | 0.006 | 1.1 |
| | | post-1 | 0.006 | 10 |
| | | post-2 | 0.023 | 10 |
| | | post-3 | 0.120 | 10 |
| 4 | 14 mo | pre-vac | 0.020 | 3.0 |
| | | post-1 | 0.020 | 5.1 |
| | | post-2 | 0.020 | 3.8 |
| 5 | 19 mo | pre-vac | 0.060 | 8.0 |
| | | post-1 | 0.12 | 10 |
| | | post-2 | 0.76 | 10 |
| 6 | 26 mo | pre-vac | 0.020 | 6.9 |
| | | post-1 | 0.060 | 10 |
| | | post-2 | 0.94 | 10 |
| 7 | 27 mo | pre-vac | 1.4 | 6.1 |
| | | post-1 | 7.4 | 10 |
| | | post-2 | 21 | 10 |
| 8 | 28 mo | pre-vac | 0.020 | 8.7 |
| | | post-1 | 0.63 | 10 |
| | | post-2 | 8.0 | 10 |
| 9 | 18 mo* | pre-vac | 1.9 | 0.11 |
| | | post-1 | 2.9 | 10 |
| | | post-2 | 11 | 10 |

*First injection of DTd-PRPvs given simultaneously with diphtheria toxoid protein vaccine in a separate site

6.5. CONJUGATION OF CAPSULAR POLYMER FRAGMENTS OF STREPTOCOCCUS PNEUMONIAE TO CRM$_{197}$

Several other bacteria resemble *H. influenzae* b in that they cause sepsis and meningitis, particularly in infants; they have polymer capsules, antibodies to which are protective; and their capsular polymers are immunogenic in mature humans but not in infants. An important example is *Streptococcus pneumoniae* (Sp) serotype 6. It causes not only the life-threatening infections mentioned above but also is a highly prevalent cause of otitis media in children. (Grey et al, Journal of Infectious Diseases, Volume 142, pages 923-33, 1980).

The approach described for PRP is also applicable to any capsular polymer in which reducing groups can be generated by selective hydrolysis with retention of antigenic specificity. In the following non-limiting example, capsular polymer fragments were made from the Sp. 6 capsular polymer by selective acid hydrolysis and were conjugated to CRM$_{197}$. The produced retained antigenic specificity for both the Sp capsular polymer and the CRM$_{197}$ component.

Generation of Reducing Fragments From Capsular Polymers (CP)

1. A sample of the CP of Sp. 6 (Danish type 6A, Eli Lilly Co.) was assayed for total hexose by the phenol-sulfuric acid method standardized with D-glucose and for reducing activity by the alkaline ferricyamide method also standardized with D-glucose.
2. A Pyrex tube received 3.3 mg Sp. 6 CP dissolved with 0.66 ml water. The sample was chilled to 0° C., 0.073 ml of 0.1N HCl were added, and the tube was sealed.
3. The tube was immersed 10 minutes in a boiling water bath, then rechilled to 0° C. A small sample was assayed for reducing activity as described in step 1:

| CP | Time heated at 100° C. | Total hexose/ reducing hexose |
|---|---|---|
| Sp. 6 | 0 minutes | 350 |
| | 10 minutes | 6.5 |

4. The hydrolyzed preparation (minus the 2% used for assay) was lyophilized. The dried material was dissolved with 0.1 ml water, transferred to microcentrifuge tube, and lyophilized again.

Conjugation to CRM$_{197}$

1. To the re-dried hydrolystate was added 0.004 ml of 2M potassium phosphate buffer pH 8 and 1 mg of CRM$_{197}$ dissolved in 0.2 ml of 0.01M sodium phosphate buffer pH 7. The resulting mixture was lyophilized and resuspended with 0.05 ml water (estimated total volume 0.063 ml).
2. To the tube was added 0.007 ml of sodium cyanoborohydride at 200 mg/ml, and the preparation was incubated 18 days at 37° C.
3. 0.6 ml 80% saturated ammonium sulfate (SAS) was added.
4. The tube was incubated 1 hour at 0° C. and centrifuged 15 minutes at 8000 G; the supernate was removed.
5. The precipitate was washed by suspension in 0.6 ml of 80% SAS buffered at pH 8 with 0.01M sodium phosphate, followed by centrifugation 15 minutes at 8000 G.
6. The precipitate was suspended with 0.02 ml of 0.5M Na$_2$HPO$_4$ and 0.2 ml 9.5M urea.
7. 1 ml SAS was added, the precipitate was isolated as in step 4 and suspended in urea at about 8M as in step 6.
8. The suspension was centrifuged 15 minutes at 8000 G.
9. The supernate was separated and dialyzed against 0.01M sodium phosphate buffer pH 7 at 4° C.
10. The dialyzed preparations, designated CRM$_{197}$-Sp. 6 was assayed for the following:
protein by the Folin phenol reaction;
Sp antigenicity by inhibition of binding of antibody to radiolabeled Sp CP (as described for PRP in Table 3);
CRM$_{197}$ antigenicity by the inhibition of antibody binding to diphtheria toxoid (DT) (as described in step o of the description of CRM$_{197}$-PRP-S#2); and
anti-CP immunogenicity by inhibition of the binding of antibody to diphtheria toxoid (DT) (as described in step p of the description of CRM197-PRP-S#2). See Table 7.

| Preparation | ng CP equivalance/ ug Protein | ug DT equivilance/ ug protein |
|---|---|---|
| CRM197 Sp. 6 | 0.4 | 0.36 |

TABLE 10

ANTI-CP IMMUNOGENIC RESPONSE OF WEANLING RABBITS WITH CONTROLS AND CONJUGATES OF *STREPTOCOCCUS PNEUMONIAE* SEROTYPE 6 FRAGMENTS OF CRM197

| Rabbit | Vaccinated With* | Percent $^{14}$C-CP Bound in Samples at age** | | | |
|---|---|---|---|---|---|
| | | 6 wk | 8 wk | 10 wk | 11 wk |
| 1 | Sp 6 CP, 25 ug | 6 | 6 | 7 | 7 |
| 2 | Sp 6 CP, 25 ug | 6 | 13 | 13 | 11 |
| 3 | Sp 6 bacteria 25 ug | 4 | 10 | 12 | 16 |
| 4 | Sp 6 bacteria 25 ug | 8 | 12 | 22 | 21 |
| 5 | CRM197 Sp 6, 25 ug | 4 | 6 | 30 | 49 |
| 6 | CRM197 Sp 6, 25 ug | 4 | 8 | 30 | 54 |

*Injected subcutaneously just prior to taking serum samples. Serum samples were taken at age 6, 8 and 10 weeks.
**25 ul serum incubated with 2 nCi $^{14}$C-labelled CP.

6.6
PRODUCTION OF PRP-CONJUGATE VACCINES BY PERIODATE OXIDATION

6.6.1.
PERIODATE OXIDATION OF PRP

Three ml of a 20 μmole/ml ribose solution were cooled to 4° C., when 0.4 ml of 2M phosphate buffer, pH 8.0, and 18 mg of sodium metaperiodate in 0.6 ml of water were added with rapid mixing. Following incubation overnight in the dark at 4° C., the reaction mixture was applied to a 1.5×90 cm Biogel P-10 column and eluted with 0.2M triethylammonium acetate buffer, pH 8.0, at a flow rate of 9 ml/hr. Aliquots of the 4.2 ml fractions that were collected were analyzed for ribose, by the orcinol assay [reference], and for reducing groups, by the Park-Johnson assay [reference]. Based upon these analyses, sets of fractions were pooled which showed average degrees of polymerization (DPs) of 6 and 10 (or other desired values), and the pools were lyophilized.

6.6.2.
DIPHTHERIA TOXOID-PRP CONJUGATION

A 72 μl aliquot of diphtheria toxoid (8.4 n 0.5 ml of water) was mixed with 1.4 μmoles of re u n groups, in the form of the lyophilized DP 6 or 10 pool, in a glass test tube. Eight μl of 2M, pH 8.0, phosphate buffer were added, the solution was vortex-mixed until homogeneous, and 2 μl of 0.4 g/ml aqueous sodium cyanoborohydride were added. After 5 days of incubation at 37° C., 300 μl of saturated ammonium sulfate were added and the mixture was allowed to stand overnight at 4° C.

The precipitated mixture was then centrifuged for 30 minutes at 4° C. and at 12,000×g, the supernatant fluid was removed, and the pellet was suspended in 500 μl of 80% ammonium sulfate. Following a second period of centrifugation, the pellet was dissolved in 500 μl of saline solution and dialyzed against saline solution for 8 hours at 4° C. Analysis of the dialysate for ribose by orcinol assay and for protein by the method of Lowry et al. [reference] revealed that the DP 6 conjugate contained 511 μg of protein, with 51.5 moles of ribose/mole of protein. The DP 10 conjugate similarly processed contained 315 μg of protein, with 59 moles of ribose/mole of protein.

6.6.3.
LT-BNT- AND CRM-PRP CONJUGATION

One mg of lyophilized LT-BNT (prepared as described in Sections 6.7–6.10) or CRM protein was dissolved in 70 μl of water and 10 μl of phosphate buffer, pH 8.0, and combined with 25 μl of 0.06 μmole/μl reducing groups in the form of DP 10 or DP 20 PRP oligosaccharides. After the addition of 2 μl of 0.4 g/ml sodium cyanoborohydride with mixing, the mixture was incubated at 37° C. for 3 days. The mixture was then transferred to a Centricon ultrafiltration cell (Amicon Instruments, Danvers, Mass., 30,000 MN cut-off) in 2 ml of saline solution and centrifuged at 6000×g at 4° C. until only 200 μl of solution remained above the membrane. The process was repeated with 2 ml of fresh saline solution, and then the conjugate was subjected to ultrafiltration with 5M urea in phosphate-buffered saline, pH 7.4, until the filtrate tested negative for ribose. The retentate was concentrated by ultrafiltration to a 0.5 ml volume and analyzed for ribose and protein, whose values may be seen in Table 11.

TABLE 11

CONJUGATION OF PRP PERIODATE OXIDATION FRAGMENTS TO CRM AND TO LT-BNT

| Carrier Protein | PRP Fragment (DP) | Yield (%) | Product Composition (μg ribose/μg protein) |
|---|---|---|---|
| CRM | 20 | 38 | 5.6 |
| CRM | 10 | 48 | 4.1 |
| LT-BNT | 20 | 98 | 1.4 |
| LT-BNT | 10 | 98 | 1.2 |

6.6.4.
IMMUNE RESPONSE TO PRP-PROTEIN CONJUGATE VACCINES

The periodate oxidation conjugate vaccines of Section 6.6.3 were diluted in saline solution and administered subcutaneously to 6–8 week old Balb/c mice or to 12-week old New Zealand white rabbits, in the dosages indicated in Table 12. Booster vaccinations were given at weekly intervals at the initial dose, and 3 weeks after initial challenge blood samples were examined by radioimmunoassay (Section 6.1) for the presence of anti-PRP antibodies. The data shown in Table 12 represent the geometric mean titer values for 4 experimental animals.

TABLE 12

IMMUNOGENICITY OF PERIODATE-PRODUCED PRP-PROTEIN CONJUGATE VACCINES

| Conjugate | | Dose (ug PRP) | Species | Anti-PRP Antibodies at week 3 (ug/ml) |
|---|---|---|---|---|
| Carrier Protein | PRP Fragment (DP) | | | |
| CRM | 10 | 1 | mouse | 0.31 |
| CRM | 10 | 10 | mouse | 1.40 |
| CRM | 20 | 1 | mouse | 0.80 |
| CRM | 20 | 10 | mouse | 2.36 |
| LT-BNT | 10 | 1 | mouse | 0.16 |
| LT-BNT | 10 | 10 | mouse | 0.12 |
| LT-BNT | 20 | 1 | mouse | 0.91 |
| LT-BNT | 20 | 10 | mouse | 0.16 |
| CRM | 10 | 2.5 | rabbit | 2.05 |

TABLE 12-continued
IMMUNOGENICITY OF PERIODATE-PRODUCED PRP-PROTEIN CONJUGATE VACCINES

| Conjugate | | | | Anti-PRP |
|---|---|---|---|---|
| Carrier Protein | PRP Fragment (DP) | Dose (ug PRP) | Species | Antibodies at week 3 (ug/ml) |
| CRM | 20 | 2.5 | rabbit | 1.80* |
| LT-BNT | 10 | 2.5 | rabbit | 0.90* |
| LT-BNT | 20 | 2.5 | rabbit | 3.60* |

*Values for these points are the geometric mean titer values for 2 experimental animals; all other values are based on the data from 4 animals.

6.7.
GENERAL PROCEDURES FOR RECOMBINANT PLASMID PREPARATION

In the present invention, the source of the LT-BNT gene was *E. coli* 711 (10407), a K-12 transconjugant containing the LT-ST plasmid of a human enterotoxigenic isolate, H10407. This strain was derived by phenotypically tagging the enterotoxin plasmid of *E. coli* H10407 by transposition from an F'ts lac::Tn5 plasmid and conjugally transferring the Tn5-tagged plasmid to *E. coli* K-12 strain 711.

The plasmid was cleaved by a restriction enzyme to yield a small DNA fragment containing the LT gene. The DNA fragment was then ligated into a pBR322 plasmid, to produce a plasmid designated pDF82. *E. coli* K-12 transformants harboring the plasmid were then selected on the basis of antibiotic resistance markers. LT production by the transformants was established through the use of an enzyme-linked immunosorbent assay and an adrenal cell assay system.

The cloned LT-B DNA region was identified and then twice recloned, first into a pBR322 plasmid to give plasmid pDF87, and then into the M13-derived cloning vector pUC8. The resultant recombinant plasmid, pJC217, was cloned after transformation into *E. coli* K-12 and selection by antibiotic resistance and the loss of an enzymatic activity marker. LT-BNT recovered from pJC217, which was immunologically indistinguishable from pDF87 and native LT-B but completely non-toxic, was then isolated from host cell lysates for use as an immunogen.

A detailed description of each step in the construction follows.

6.7.1.
CONDITIONS FOR RESTRICTION ENZYME DIGESTIONS

The restriction enzymes used were the products of Bethesda Research Laboratories, Inc., Gaithersburg, Md. A unit of enzyme activity is defined as the amount of enzyme required to completely digest 1.0 µg of lambda DNA in one hour at an appropriate temperature and in a 50 µl total reaction mixture volume.

Digestions were carried out by incubating 2 µg of DNA with 10 units of enzyme at 37° C. for 30 minutes in 20 µl of buffer. Reactions were stopped by heating to 70° C. for 5 minutes, and the overall conditions produced one cleavage per vector plasmid DNA molecule. For Pst I and Hind III, the buffer consisted of 50 mM Tris-HCl (pH 8.0), 10 mM MgCl₂ and 50 mM NaCl. Other reactions were carried out essentially as described by the manufacturer.

6.7.2.
PURIFICATION OF DNA DIGESTION PRODUCTS

Following restriction enzyme treatment of pDF87, the digestion mixture was subjected to electrophoretic separation in vertical gel slabs containing 1.2% low melting point agarose in 40 mM Tris, 0.2M sodium acetate and 2 mM EDTA (pH 7.8). Electrophoresis was carried out at 10 volts per cm, and the slabs were then stained with ethidium bromide and visualized under ultraviolet light, as described by Bolivar and Backman [Methods in Enzymology 68: 245 (1979)].

The separated DNA fragments were then excised from the gel, the gel was melted, and the LT-B DNA fragment was extracted with phenol.

6.7.3.
T4 DNA LIGATION

Ligation reactions were carried out with T4 DNA ligase from Bethesda Research Laboratories, Inc., Gaithersburg, Md. A unit of T4 DNA ligase activity is defined as the amount required to catalyze the conversion of 1 nmole of $^{32}$PPi into $[\alpha/\beta^{32}P]$-ATP at 37° C. in 20 minutes.

DNA ligations were performed using 10 units of enzyme per µg of DNA at 4° C. for 18 hours. The buffer contained 66 mM Tris-HCl, 6.6 mM MgCl₂, 10 mM dithiothreitol and 66 µM ATP at pH 7.6.

To reduce recircularization, in some cases plasmid pBR322 was treated with alkaline phosphatase conjugated to Sepharose before ligation. The enzyme used was MATE-BAP from Bethesda Research Laboratories, Inc., Gaithersburg, Md. One unit of MATE-BAP is defined at the amount of enzyme that hydrolyzes 1 nmole of ATP in 30 min. at 37° C. The enzyme was used at a concentration of 500 units per µg of DNA at 65° C. for 1 hour in 10 mM Tris-HCl, pH 8.0. Following reaction, the enzyme was removed by centrifugal pelleting.

6.7.4.
TRANSFORMATION AND ISOLATION OF RECOMBINANTS

The transformation of *E. coli* K-12 strains was carried out as described by Bolivar and Backman [Methods in Enzymology 68: 245 (1979)]. Cells were made competent by incubation in 30 mM CaCl₂ at 0° C. for 20 minutes. Then 0.2 ml aliquots of 10X concentrated cells were added to DNA in 0.1 ml of cold ligation buffer supplemented with 30 mM CaCl₂ and incubated at 0° C. for 1 hour. The cells were then heated to 37° C. for 2 minutes, held at room temperature for 10 minutes, and diluted into 4 ml of Luria broth (L broth). Per liter, L broth contains 10 g of Bacto tryptone, 5 g of Bacto yeast extract, and 10 g of NaCl, all adjusted to pH 7.5 with 1M NaOH.

After 3 hours of incubation at 37° C., transformants were selected on Trypticase soy agar [BBL Microbiology Systems, Cockeysville, Md.] or YT plates, using appropriate antibiotics or enzymatic activity markers as described infra.

6.8. METHODS FOR LT GENE PRODUCT ANALYSIS

At each stage of the cloning procedure, the *E. coli* K-12 transformants were analyzed for the quality and quantity of LT or LT-B production by enzyme-linked immunosorbent assay (ELISA). To determine the toxicity of their gene products, the transformants were also analyzed by a mouse adrenal cell assay system in which cells exposed to enterotoxigenic *E. coli* or to their toxins exhibit readily detectable morphological changes.

6.8.1. ENZYME-LINKED IMMUNOSORBENT ASSAY (ELISA)

As described by Clements et al. [Infect. Immuno. 40: 653 (1983)], clones to be analyzed were cultured overnight at 37° C. in 20 ml of Trypticase soy broth [BBL Microbiology Systems, Cockeysville, Md.], centrifuged, suspended in 2 ml of buffer containing 0.05M Tris, 0.001M EDTA, 0.003M sodium azide and 0.2M NaCl [pH 7.5], and disrupted by sonication with a Branson sonicator for 12 seconds at a power setting of 100–150 watts. The resultant lysates were clarified by centrifugation and serially diluted in pH 7.4 phosphate-buffered saline containing 0.05% Tween 20 (PBS-Tween) for analysis.

ELISA was carried out using two basic methods. In one method the wells of polystyrene microtiter plates [Costar, Cambridge, Mass.] were precoated with 50 µg per ml of type III gangliosides [Sigma Chemical Co., St. Louis, Mo.] to improve the binding of the LT-B subunit and, hence, to increase sensitivity. The microtiter wells were then filled with 0.2 ml aliquots containing the diluted lysate samples and incubated for 1 hour at room temperature. Following the incubation, the microtiter wells were emptied and washed three times with PBS-Tween. The wells were then treated successively for one hour each at room temperature with monospecific goat hyperimmune antiserum to LT [Clements et al., Infect. Immun. 29: 91 (1980)] and with rabbit anti-goat antiserum conjugated to alkaline phosphatase [Miles Research Laboratories], with three PBS-Tween washings following each addition.

Alkaline phosphatase analysis was then performed by adding 200 µl aliquots of 1 mg/ml p-nitrophenyl phosphate substrate in 10 percent diethanolamine buffer (pH 9.8), incubating the plates for 60 minutes at room temperature, stopping the reactions by the addition of 25 µl aliquots of 3M NaOH, and measuring the results spectrophotometrically at 400 nm.

In some cases, a modification of the ELISA method of Holmgren and Svennerholm [Scand. J. Immunol. 8, Suppl. 7: 111–118 (1978)] was used instead. Microtiter plates were precoated with type III gangliosides, and 100 µl aliquots of samples to be tested in PBS with 0.5% gelatin (PBS-G) were pipetted into the microtiter wells. The plates were then incubated at 37° C. for 45 minutes, the wells were filled with PBS-G, incubation was continued for another 30 minutes at 37° C., and the plates were washed with PBS-Tween. The wells were then treated successively for 45-minute periods at 37° C. with 100 µl aliquots of PBS-G containing first antiserum to LT, and then antiserum directed against the anti-LT immunoglobulins that had been conjugated to horseradish peroxidase. Following each incubation period, the wells were washed three times with PBS-Tween.

Horseradish peroxidase analysis was then carried out with the use of o-phenylenediamine as a substrate. The substrate was prepared immediately before use by dissolving 1 mg of o-phenylenediamine (Sigma Chemcial Co., St. Louis, Mo.) per 1 ml of 0.1M sodium citrate buffer, pH 5.0. Then, an equal volume of a solution containing 1 ml of 0.3% $H_2O_2$ per 50 µl of the citrate buffer was added to yield a final 0.006% $H_2O_2$ concentration. Two hundred µl of the substrate was added to each well, the plates were incubated for 30 minutes at room temperature in the dark, and the peroxidase reaction was stopped by the addition to each well of 75 µl of 4M $H_2SO_4$. The results were determined spectrophotometrically by measuring absorbance at 492 nm.

ELISA employing horseradish peroxidase was considerably more sensitive than that using alkaline phosphatase. In other respects, however, the two systems were comparable.

6.8.2. Y1 ADRENAL CELL ENTEROTOXIN ASSAY

Clarified cell lysates, prepared as described in Section 6.8.1., supra, were analyzed for toxicity in the mouse Y1 adrenal cell system of Sack and Sack [Infect. Immun. 11: 334 (1975)]. Y1 adrenal cells maintained in Ham's F10 medium with 12.5% horse serum, 2.5% fetal calf serum, and 40 µg per µl gentamycin were subcultured into 75 $cm^2$ culture dishes containing the same medium and incubated at 37° C. until the cells reached confluency.

Once the cells were confluent, the medium was replaced by fresh medium containing serially diluted aliquots of the *E. coli* LT-B clone lysates, and the cultures were incubated further. After 18 to 24 hours of incubation, the cultures were examined with a phase contrast inverted microscope for cell morphology. Under the influence of LT toxin, the normally flat adrenal cells become rounded. The sensitivity of the assay is such that as little as 0.2 µg of crude *E. coli* toxin or 10 pg of purified LT per 200 µl of medium may be detected.

6.8.3. RAT ILEAL LOOP ASSAY OF ENTEROTOXIN ACTIVITY

Using the method of Klipstein and Engert [Infect. Immun. 23: 592–599 (1979)], weanling Sprague-Dawley rats (Charles River Breeding Laboratories, Wilmington, Mass.) were surgically prepared by exposing the ileum and ligating 10-cm loops at the distal portion. Each animal was then challenged by direct inoculation with LT, LT-B or LT-BNT in 0.5 ml of sterile saline solution into the loop.

After 18 hours, the animals were sacrificed and the loops were examined for fluid accumulation. Data derived from the values from 5–8 rats at each enterotoxin concentration were expressed as fluid accumulation per centimeter of ileum. A positive response, denoted by a fluid accumulation of more than 50 µl/cm of ileum, was observed with as little as 1 µg of LT.

6.9.

PREPARATION AND ISOLATION OF SPECIFIC LT-B-PRODUCING CLONES

Because of toxicity in the LT-B produced by the first clones, the LT-B gene was successively transferred into plasmid pBR322 and then into the M13mp7-derived pUC8 plasmid [Vieira and Messing, Gene 19: 259 (1982)].

6.9.1.

ISOLATION OF pDF82

The LT+ST+ enterotoxin plasmid of human isolate H10407 was cleaved with the restriction enzyme Pst I, to yield a 5.2 Kb DNA fragment (see FIG. 1). This fragment, which contained the LT gene, was then inserted into plasmid pBR322 which had been cut with Pst I and treated with alkaline phosphatase. Ligation was carried out with T4 DNA ligase to produce a 10.4 Kb plasmid, designated pDF82. The ligation mixture was then used to transform E. coli MM294.

Plasmid pBR322 encodes both ampicillin and tetracycline resistance. When the plasmid is cut by the restriction enzyme Pst I and a DNA fragment is inserted, ampicillin resistance is lost, but not tetracycline resistance. These transformants were thus isolated by screening for ampicillin sensitivity ($Ap^s$) and tetracycline resistance ($Tc^r$) by growth, or inability to grow, in medium containing these antibiotics. After plating on Trypticase soy agar containing 25 μg per ml tetracycline, the cultures were incubated for 18 hours at 37° C. Growing colonies were then cloned in L broth, aliquots were spotted on Trypticase soy agar plates containing 100 μg per ml ampicillin and incubated for 18 hours at 37° C.

$Ap^sTc^r$ transformants were then assayed for LT production by the Y1 adrenal cell system and ELISA. Plasmid DNA was isolated from several LT+ transformants by the method of Bolivar and Backman [Methods in Enzymology 68: 245 (1979)] and subjected to electrophoresis in 0.7% agarose. The conditions for electrophoresis and DNA visualization were as described in Section 6.6.2. above. One isolate, designated pDF82, was positive in both assay systems and showed only a single plasmid upon electrophoresis.

When recut with Pst I, plasmid pDF82 yielded only two fragments that corresponded to the 4.3 Kb pBR322 cloning vector and the 5.2 Kb LT-encoding DNA fragment. Subsequent analysis of the recombinant plasmid with Pst I, Eco RI, Hind III, Hinc II, Hinf I and Ava II confirmed the size of the DNA fragment and the absence of internal Pst I sites.

6.9.2.

ISOLATION OF pDF87

Figure 2:
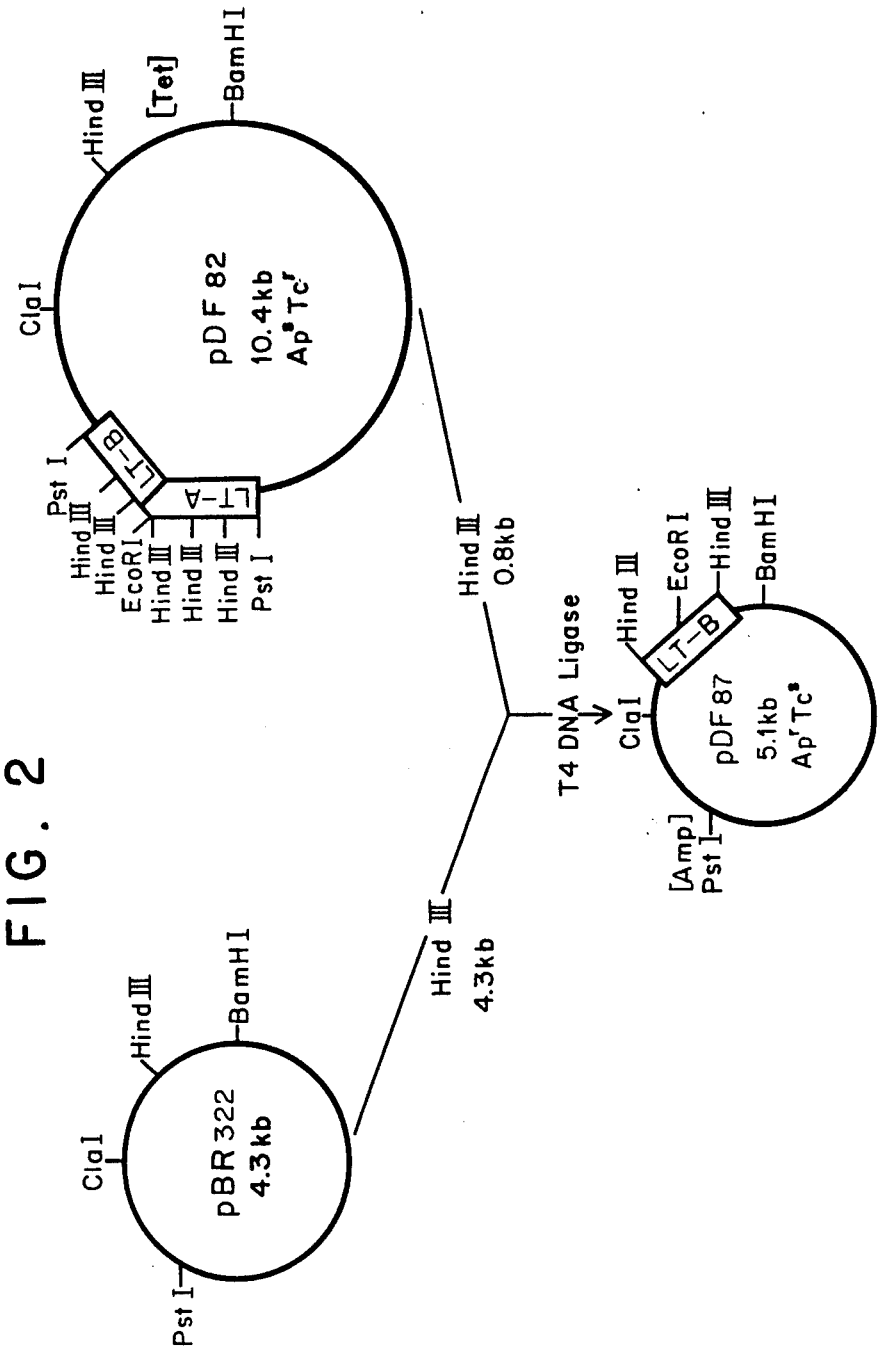
FIG. 2 is a schematic representation of the construction of plasmid pDF87, through the insertion into the single HindIII site of pBR322 of a 0.8 kb fragment containing the LT-B gene and derived from plasmid pDF82 by HindIII excision.

The cloned LT DNA region from pDF82 was recloned into the single Hind III site in the tetracycline resistance gene of plasmid pBR322 (see FIG. 2). Plasmids pDF82 and pBR322 were cut with Hind III, mixed and joined by T4 DNA ligase. The ligation mixture was again transformed into E. coli MM294, and transformants were selected on the basis of antibiotic resistance and sensitivity.

Because Hind III cleavage and DNA fragment insertion destroys tetracycline resistance but does not affect ampicillin resistance, $Ap^rTc^s$ cells were selected for. This was accomplished by a selection approach that was further enhanced by the use of cycloserine, which kills multiplying E. coli cells. After 18 hours of incubation in L broth with 50 μg/μl ampicillin, the culture was diluted 1:100 into fresh medium containing 4 μg per ml tetracycline. After 45 minutes of incubation, D-cycloserine was added to a concentration of 100 μg per ml, and incubation was continued for an additional 2 hours.

The culture was then centrifuged, and the pellet was resuspended in 20 ml of L broth. After 3 hours of further incubation, 0.1-ml aliquots were plated on Trypticase soy agar with 50 μg per ml ampicillin, and the resultant colonies were isolated. The transformants were then assayed for the production of LT-B by ELISA and for the absence of LT-A by lack of toxicity in the Y1 adrenal cell assay. One clone largely meeting these requirements but retaining 1/1000 of the toxicity of LT from pDF82, on a weight basis, was designated pDF87. The reason for this toxicity was unclear, since no LT-A could be detected in pDF87 by SDS polyacrylamide gel electrophoresis, ELISA, or gel filtration under dissociating conditions.

Treatment of pDF87 with Hind III split the DNA into two fragments—pBR322 and a smaller (0.8 Kb) fragment coding for LT-B. Significantly, the 1.5 Kb Hind III gene fragment that codes for the production of LT-A was absent.

6.9.3.

ISOLATION OF pJC217

Figure 3:
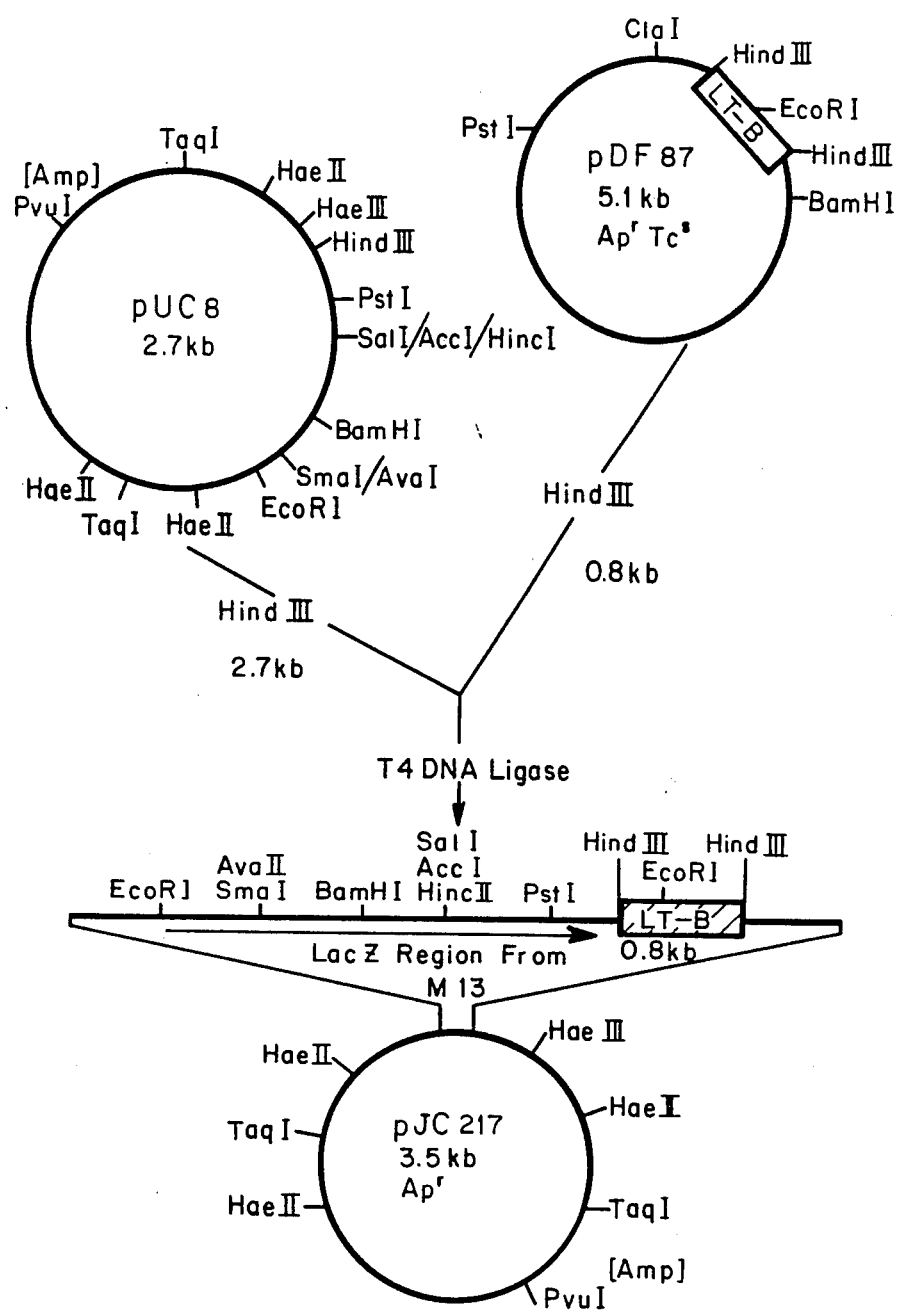
FIG. 3 is a schematic representation of the production of plasmid pJC217 by insertion into the single HindIII site of pUC8 of a 0.8 kb fragment containing the LT-B gene and derived from plasmid pDF87.

The cloned LT-B DNA from pDF87 was recloned into the single Hind III site of cloning vector pUC8 (see FIG. 3). This vector, constructed by Vieira and Messing [Gene 19: 259 (1982)], is derived from M13mp7. Plasmid pDF87 was cut with Hind III, and the 0.8 Kb LT-B DNA fragment was separated by electrophoresis in low melting point agarose (see section 6.7.2, supra) and extracted with phenol. pUC8 was then cleaved with Hind III, mixed with the purified LT-B gene fragment, ligated and transformed into an E. coli K-12. Insertion of DNA fragments at the Hind III site of PUC8 disrupts the structural gene for β-galactosidase activity which, together with unaltered ampicillin resistance in the plasmid, provides a basis for transformant selection.

Transformants were plated on YT plates (8 g Bacto Tryptone, 5 g NaCl, 5 g Yeast Extract and 1.5 g agar per liter of water) containing 100 μg per ml of ampicillin and supplemented with 200 μg per ml of 5-bromo-4-chloro-3-indoyl-β-D-galactoside (X-gal). As described by Rüthere [Mol. Gen. Genet. 178: 475 (1980)], Xgal is a β-galactosidase substrate that in the presence of the enzyme turns from colorless to blue. Following incubation for 18 hours at 37° C. on Xgal-YT, colorless colonies (whose plasmid-associated β-galactosidase activity had been insertionally inactivated) were isolated.

The $Ap^r$ β-galactosidase⁻ transformants were then assayed by ELISA for LT-BNT production. LT-BNT from one positive clone, designated pJC217, was then tested in Y1 adrenal cells, where it was found to be completely non-toxic. The bacterium harboring this plasmid was designated E. coli strain JM83 (pJC217).

6.10. RECOVERY OF LT-BNT

6.10.1. GROWTH OF E. COLI K-12 CONTAINING THE pJC217 PLASMID

Subculturing of strain JM83 (pJC217) produces two types of colonies. One, designated type O, is small, raised and opaque in appearance. The other, designated type T, is larger, flat and translucent. It is important for the production of LT-BNT to utilize only type T colonies, since they produce 50–100 times as much LT-BNT as type O colonies. Because type O colonies can arise spontaneously from the T type, a single type T colony should be selected.

The choice of medium for the propagation of *E. coli* strain JM83 (pJC217) is not critical, and Trypticase soy broth, ML medium and the CAYE medium of Evans will suffice. In one embodiment of this invention, the organism transformed by plasmid pJC217 was streaked confluently on a 10×1.5 cm culture dish containing Trypticase soy agar with 100 µg/ml of ampicillin, to stabilize the plasmid. After incubation for 18 hours at 37° C., each plate contained a sufficient quantity of cells to serve as an innoculum for 10 liters of growth medium.

After the incubation, bacteria from the Trypticase soy agar plates were harvested with 5 ml of sterile 0.85 percent NaCl and used to inoculate CAYE medium with 0.5% glucose at a level of approximately $10^6$ CFU per ml. CAYE medium consists of 20 g of Casamino Acids, 6 g of Yeast Extract, 2.5 g of NaCl, 8.71 g of $K_2HPO_4$ and 1 ml of trace salts (5% $MgSO_4$, 0.5% $MnCl_2$ and 0.5% $FeCl_3$) per liter of distilled water. Following inoculation, the cultures were incubated with agitation at 37° C. for 18–24 hours.

6.10.2. CELL DISRUPTION

Cells from the incubation medium were collected by centrifugation at 5,000 xg for 20 minutes at 4° C. The supernatant fluids were discarded into Clorox disinfectant, and the cell pellets were suspended in a minimal volume of buffer containing 0.05M Tris, 0.001M disodium EDTA, 0.003M sodium azide, and 0.2M NaCl, pH7.5 (TEAN buffer). These cell suspensions were then pooled and stored frozen at −60° C. until needed.

The freezing of the cells generally provides sufficient disruption of *E. coli* K-12 for LT-BNT recovery. Mechanical disruptive techniques such as the use of sonication or a French press could be applied as long as scrupulous care was taken to avoid the generation of heat in the sample. Lysozyme should be avoided, since final LT-BNT recoveries with it as a lytic agent were decreased by 60 percent.

By swirling the storage containers for a minimum time in a 37° C. water bath, the frozen cell suspensions were rapidly thawed. The suspensions were then combined with an equal volume of TEAN buffer, swirled gently to mix, and then centrifuged at 5,000 xg for 20 minutes at 4° C. to sediment membranes and unlysed cells. Typical recovery of LT-BNT from a single application of this freeze-thaw procedure was 50 percent. Further recovery could be made by either repeating the cycle or by applying other disruptive techniques to the more refractory unlysed cells. All supernatant fractions from the centrifugation steps were then combined for further purification.

6.10.3. AFFINITY CHROMATOGRAPHIC PURIFICATION OF LT-BNT

The clear supernatant fluids from the centrifuged cell lysates were applied directly (not layered under buffer) to the top of a 2.5×80 cm Sepharose 4B [Pharmacia Fine Chemicals, Piscataway, N.J.] column which had previously been equilibrated in TEAN buffer at 4° C. The column was then purged with TEAN buffer at a flow rate of 20 ml per hour until effluent monitoring at 280 nm reached the baseline level. At that point, 0.2M galactose in TEAN buffer was applied and maintained at a flow rate of 20 ml per hour, while 6 ml fractions were collected. The emergence of LT-BNT was detected as a single peak of absorbance at 280 nm that slightly preceded the galactose front.

All operations were carried out at 4° C., and when complete, LT-BNT fractions were pooled, dialyzed against large volumes of TEAN buffer and lyophilized for storage.

6.11. ANALYSIS OF LT-BNT FOR TOXICITY

Samples of LT, LT-B from clone pDF87, and LT-BNT from clone pJC217 were analyzed in the Y1 adrenal cell assay system as described supra, in Section 6.8.2. The protein content of the samples was determined by the method of Lowry et al. [J. Biol. Chem. 193: 265–275 (1951)]. The results are shown in Table 13.

TABLE 13

| Adrenal Cell Assay of Enterotoxin Activity | |
|---|---|
| Preparation | Biological Activity* |
| LT | 0.038 |
| LT-B (pDF87) | 39 |
| LT-BNT (pJC217) | 25,000 |

*Activity is expressed as the nanogram quantity of each preparation required to produce the rounding of 50% of the cells.

The data of Table 13 indicate that the toxicity of LT-BNT is drastically reduced compared to that of LT, with LT being greater than 650,000 times more active than LT-BNT. The results for LT-B show that it, while substantially less toxic than LT, retains considerable toxicity. This toxicity, which is comparable to that of the B subunit produced by the chromatographic separation of the complete LT enterotoxin into its subunits, renders ordinary LT-B unsuitable for use as a vaccine.

Analysis of LT and LT-BNT in the rat ileal loop assay, as described in section 6.8.3, also revealed the remarkable non-toxic character of LT-BNT. The results are shown in Table 14, wherein each value is the average from 5–8 rats.

TABLE 14

| Rat Ileal Loop Assay of Enterotoxin Activity | | |
|---|---|---|
| Preparation | Amount (µg) | Fluid Accumulation* Ratio (µl/cm of ileum |
| LT | 1 | 65 |
| LT | 10 | 421 |
| LT | 100 | 818 |
| LT-BNT | 100 | 0 |

*Fluid Accumulation Ratios greater than 50 are considered to be a positive result.

As shown in Table 14, a 100 μg quantity of LT-BNT was completely inactive in the rat ileal loop assay. In contrast, the same quantity of LT produced a stimulation of ileal loop fluid accumulation that was more than 16 times the minimally significant level.

6.12.
PREPARATION OF ANTISERUM AGAINST LT-BNT

6.12.1.
PREPARATION OF ANTISERUM AGAINST LT-BNT IN MICE

Groups of 10 Balb/cj female mice (Jackson Laboratories), 4–6 weeks of age, were injected subcutaneously with 0.1 ml of saline solution (9 g NaCl/liter distilled water), either alone as a control or with a quantity of LT-BNT added. In some cases a booster injection was administered one week later. Immediately before vaccination and at varying times thereafter, blood specimens were obtained by tail snipping, and the serum was diluted and assayed for antibody activity by ELISA, as described supra, in Section 6.8.1. Antibody activity is expressed as the overall sample dilution needed to produce an absorbance falling in the linear region of the absorbance curve.

In a preliminary experiment, the effects of vaccination with varying quantities of LT-BNT were observed. The results are shown in Table 15.

TABLE 15
Dose Response Following Vaccination of Mice With LT-BNT

| LT-BNT | Antibody Activity | |
| DOSE (μg) | Pre-Immune | Post-Immune* |
| --- | --- | --- |
| — | ND+ | ND |
| 1 | ND | 4 |
| 10 | ND | 8 |
| 100 | ND | 192 |

+ND = Not Detectable
*Post-immune activity was examined in tail snip blood samples one week after vaccination with the quantity of LT-BNT indicated, by alkaline phosphatase ELISA. Antibody activity is expressed as the overall sample dilution needed to produce an absorbance at 400 nm falling in the linear region of the absorbance curve. Vaccination was carried out in saline solution without adjuvant.

As indicated in Table 15, antibodies against LT-BNT were not detectable in any of the animals prior to vaccination. By one week after vaccination, anti-LT-BNT antibodies could be detected. As expected, antibody activity increased with increasing exposure to LT-BNT.

To determine whether there could be a secondary antibody response to multiple vaccinations, groups of mice were injected with LT-BNT as described above, and then again one week later with a similar dose. The results are shown in Table 16.

TABLE 16
Effect of a Second Vaccination With LT-BNT on Antibody Production in Mice

| LT-BNT | Antibody Activity | | | |
| DOSE (μg) | Pre-Immune | Post-1°Immune* | Second Vaccination | Post-2°Immune* |
| --- | --- | --- | --- | --- |
| — | ND+ | ND | — | ND |
| 10 | ND | 8 | + | 7,144 |
| 10 | ND | 8 | — | 384 |

+ND = Not Detectable
*Post-immune activity was examined in tail snip blood samples one week after vaccination (1°) with LT-BNT, by alkaline phosphatase ELISA. At that time, either a second vaccination (2°) or saline solution was administered, and post-immune activity was again examined one week later. Vaccination was carried out in saline solution without adjuvant.

The data in Table 16 show that anti-LT-BNT activity could be detected only in animals that had been injected with LT-BNT. This activity increased markedly following a second challenge with LT-BNT. In contrast, when no LT-BNT booster was given, the increase in antibody titer, while substantial, was much lower.

That the antibody activity produced in response to challenge by LT-BNT was persistent was shown in an experiment in which 10 Balb/cj female mice were injected with 10 μg of LT-BNT in saline solution without adjuvant. At various times thereafter, tail snip blood samples were analyzed for anti-LT-BNT antibody activity by horseradish peroxidase ELISA. As shown in Table 17, antibody activity reached a peak at two weeks after immunization but remained substantial even after 20 weeks. This strong and persistent response was seen even though no booster was administered and no adjuvant was used.

TABLE 17
Persistence of Antibody Activity in Mice Following a Single LT-BNT Injection

| Time After Vaccination (weeks) | Antibody* Activity |
| --- | --- |
| 0 | ND+ |
| 1 | 320 |
| 2 | 10,240 |
| 4 | 5,120 |
| 8 | 1,280 |
| 20 | 640 |

+ND = Not Detectable
*Antibody activity is expressed as the degree of antiserum dilution needed to produce a response in the linear region of the ELISA absorbance curve at 492 nm.

6.12.2.
PREPARATION OF ANTISERUM AGAINST LT-BNT IN A GOAT

Antiserum was produced in an 6 month old outbred goat by injecting 2 mg of purified LT-BNT subcutaneously, using standard methods. An identical booster vaccination was given 4 weeks later, and blood samples were harvested 10 weeks after the initial vaccination. Blood thus collected was allowed to clot, the clot was sedimented by centrifugation at 5,000×g for 30 minutes, and the resulting serum was treated with 50% ammonium sulfate overnight at 4° C. The precipitate that formed was pelleted by centrifugation at 10,000×g for 5 minutes, and the pellet was dissolved in 10 ml of TEAN buffer (Section 6.10.2), and dialyzed three times for a total of 24 hours at 4° C. against 200X volumes of the same buffer.

To render the resulting antiserum highly specific for LT-BNT, the preparation was twice purified by affinity chromatography. For this purification procedure, LT-BNT-Sepharose and CT-B-Sepharose were prepared by covalently binding purified LT-BNT or CT-B (List Biological Laboratories, Inc.) to cyanogen bromide-activated Sepharose 4B (Pharmacia Fine Chemicals, Piscataway, NJ), according to the manufacturer's instructions. The dialyzed antiserum was first passed through a 1.5×18 cm column of LT-BNT-Sepharose, which was washed extensively with TEAN buffer. Immunoglobulins that had bound to the immobilized LT-BNT were then eluted from the column with 0.2M glycine-HCl buffer, pH 3.5, which was neutralized with 0.25M Tris as collected.

The eluted immunoglobulins were dialyzed against TEAN buffer as described, supra, and then applied to a 1×5 cm CT-B-Sepharose column. Immunoglobulins passing through the column were collected and were shown by ELISA to be specific for LT-BNT, but unreactive to CT-B.

6.12.3.
PRODUCTION OF MONOCLONAL ANTIBODIES

To obtain spleen cells that can be made to produce antibodies against LT-BNT, 6-8 week old Balb/c mice (Jackson Laboratories) were sacrificed and the spleens were aseptically removed. Single cell suspensions were obtained by forcing the spleens through a wire mesh (Collector, E-C Apparatus Corp., St. Petersburg, Fla). The splenocytes thus prepared were exposed to 1 µg/ml sterile LT-BNT in complete Dulbecco's Modified Eagle's Medium (DMEM) with 4,500 mg/liter glucose, 20% fetal bovine serum, 10% NCTC 109, 1% nonessential amino acids, 100 units/ml penicillin, 100 µg/ml streptomycin, 0.3 mM 8-bromoguanosine, $5\times10^{-5}$M 2-mercaptoethanol, and 50% thymocyte conditioned medium (TCM).

TCM, which is required for the successful in vitro immunization of spleen cells and which eliminates the need for feeder layers in cell cloning, was prepared by aseptically removing the thymuses from 4 to 6 week old BALB/c mice. The isolated thymuses were then disrupted as described above, the cells were cultured for three days in complete DMEM in a humidified 10% $CO_2$ incubator at 37° C., and the medium was harvested by pelleting the cells by centrifugation at 1,000×g for 10 minutes and stored frozen at −20° C. until needed.

After 4 days of incubation in 10% $CO_2$ at 37° C., the LT-BNT-treated splenocytes were recovered by centrifugation at 1,000×g for 10 minutes. To produce hybridomas, they were then mixed in a four-fold excess with murine myeloma cells (X63-Ag 8.653), and fusion was facilitated by the addition of 40% polyethylene glycol (PEG 1300, MCB Chemicals) and 5% dimethylsulfoxide. Following one minute of gentle mixing at 25° C., the suspension was slowly diluted with DMEM, and the cells were removed from the medium by centrifugation.

The cells were then suspended in complete DMEM that had been supplemented with $5\times10^{-5}$M 2-mercaptoethanol, 30% TCM and HAT ($10^{-4}$M hypoxanthine, $10^{-5}$M aminopterin, $3\times10^{-5}$M thymidine) at a dilution of $5\times10^5$ myeloma cells/ml. The cells were then cultured by distributing the suspension into 96-well tissue culture dishes, which were incubated in 10% $CO_2$ at 37° C. with twice weekly medium replacement. Visible colonies appeared in 30 to 60% of the wells after one week, and after three weeks, the supernatant medium in the wells was tested for the presence of LT-BNT-specific antibodies by horseradish peroxidase ELISA, as described in Section 6.8.1. Cells in wells whose medium was positive by ELISA were then cloned by limiting dilution or by plating in agarose.

Limiting dilution cloning was performed by diluting desired hybridoma cells to concentrations of 500, 50 and 5 cells/ml in complete DMEM supplemented with 40% TCM, and plating aliquots of the suspensions in the multiwell tissue culture dishes. Medium over the clones was then retested by ELISA after 2 to 3 weeks of incubation, and positive clones were expanded by subculturing in the same medium.

Cloning in agarose was carried out essentially as described by Coffino and Scharff [Proc. Natl. Acad. Sci. U.S.A. 68: 219-223 (1971)]. Tissue culture dishes (15×60 mm Corning) that had been coated with 4 ml of 0.4% Sea Plaque Agarose in DMEM were overlaid with 1 ml of 0.35% agarose containing 1000 cells/ml in complete DMEM supplemented with 40% TCM. The plates were incubated in a humidified 10% $CO_2$ incubator at 37° C. until the colonies reached an 8 to 16 cell size. Then, a 1 ml overlay containing 0.4% agarose in DMEM with a 1:50 dilution of anti-mouse IgM/IgG was added to each dish. After 2 to 3 days of incubation, visible precipitates marked the locations of immunoglobulin-secreting colonies, and the most vigorously secreting colonies were transferred by sterile pasteur pipette to 96-well plates. Especially strong anti-LT-BNT antibody producers were identified by ELISA, and stocks were developed through subculturing as desired. However derived, cloned cell stocks were preserved by storing frozen at −170° C. in 10% dimethyl sulfoxide with 90% fetal bovine serum.

To produce large quantities of monoclonal antibodies for use in diagnostic tests or for other purposes, the hybridoma cells were grown as ascites tumors. Eight week old BALB/c mice were primed with Pristane (0.5 ml/mouse, Aldrich Chemical Co., Milwaukee, WI), and then injected 10 days later with $10^7$ hybridoma cells. Ascites fluid, which developed in 7 to 10 days, was tapped with an 18 gauge syringe needle inserted into the abdomen of anesthetized animals. This fluid was then clarified by centrifugation at 2,000×g for 10 minutes, preserved by the addition of 0.1% sodium azide and stored at 4° C.

6.13
NEUTRALIZATION OF ENTEROTOXIN ACTIVITY BY ANTISERUM AGAINST LT-BNT

To determine whether antiserum to LT-BNT could neutralize the activity of the enterotoxins of Vibrio cholerae and E. coli, quantities of these toxins that were 100 times the amount needed to prduce cell rounding in the Y1 adrenal cell system were incubated with various dilutions of goat antiserum (Section 6.6.2) for 1 hour at 37° C. Following the incubation, the samples were analyzed for toxicity in the adrenal cell system, as described in Section 6.2.2. As shown in Table 18, the diluted antiserum to LT-BNT completely neutralized both of the enterotoxins.

TABLE 18

Neutralization of the Activities of the Cholera and E. coli Enterotoxins in the Adrenal Cell Assay by Antiserum to LT-BNT

| Enterotoxin+ | Antiserum Neutralization Titer* |
|---|---|
| Cholera toxin | 40 |

TABLE 18-continued

Neutralization of the Activities of the Cholera and E. coli Enterotoxins in the Adrenal Cell Assay by Antiserum to LT-BNT

| Enterotoxin+ | Antiserum Neutralization Titer* |
|---|---|
| E. coli LT | 1,280 |

+Enterotoxin used was approximately 100 minimal rounding doses.
*Titer is defined as the reciprocal of the highest serum dilution showing complete neutralization of biological activity.

6.14.
ANALYTICAL SYSTEMS BASED ON LT-BNT

6.14.1
ELISA ASSAY

In section 6.8.1, supra, a procedure is described for the ELISA detection of LT-BNT in samples. The ELISA system is equally applicable to the detection of specific antibodies to LT or LT-B in sera from human beings or from immunized animals. To use ELISA for antibody detection, 100 μl aliquots of 1 μg/ml LT-BNT in a coating buffer containing 50 mM sodium carbonate, pH 9.6, were pipetted into the wells of 96-well polyvinyl plates (Costar). The plates were incubated for 2 hours at room temperature, when the wells were filled with 0.5% gelatin in coating buffer and incubated overnight at 4° C. Any unattached antigen was then removed by three 3-minute washes with phosphate buffered saline containing 0.05% Tween 20 (PBS-T).

Samples containing antibodies to be analyzed, such as goat, human or mouse serum or murine hybridoma supernatant, were then diluted in PBS containing 0.5% gelatin and added in 100 μl aliquots to the antigen-coated wells. The plates were incubated for 45 minutes at 37° C., the supernatant fluids were removed, and the wells were washed three times with PBS-T. Then, a second antibody (anti-goat, -human, or -mouse immunoglobulin antiserum as appropriate) coupled to horseradish peroxidase was added to the wells in 100 μl aliquots, and the plates were incubated for 45 minutes at 37° C.

After the second-antibody incubation, the plates were washed with PBS-T, and 200 μl aliquots of substrate (1 mg O-phenylenediamine in 1 ml of 0.1M sodium citrate buffer, pH 5.0, with 0.006% $H_2O_2$) were added to the wells. After a 30 minute incubation at 25° C., the enzymatic reaction was stopped by the addition of 75 μl of 4M $H_2SO_4$. The absorbances of the contents of the wells were then measured at 492 nm. Positive samples were taken to be those whose absorbance was at least twice that of controls, to which no primary antibodies had been added.

In a demonstration of the method, serum samples were collected from children and adults and analyzed for the presence of antibodies to LT-BNT, as shown in Table 19.

TABLE 19

| Prevalence of Antibodies to LT-BNT In Human Serum | | |
|---|---|---|
| Subjects | Number Studied | Positive Cases |
| Children | | |
| 18–24 months | 10 | 2 |
| 24–36 months | 10 | 1 |
| 36–48 months | 9 | 2 |
| Adult | | |
| Pregnant Women | 10 | 2 |
| General Population | 10 | 5 |

TABLE 19-continued

| Prevalence of Antibodies to LT-BNT In Human Serum | | |
|---|---|---|
| Subjects | Number Studied | Positive Cases |
| Pediatric Health Professionals | 9 | 7 |

The data in Table 19 are based upon the analysis of blood samples taken from individuals in the indicated age categories or from health care professionals working in the Division of Pediatric Infectious Diseases at The University of Rochester Medical Center. As might be expected for children with limited exposure histories, incidences of antibodies to LT-BNT were low. Incidences were somewhat higher for the general adult population, and higher still for the pediatric health professional group. The serum of 7 of 9 individuals from the latter group was positive, a finding not unexpected in view of the high probability of their contacting patients presenting enterotoxigenic diarrheal disease.

6.14.2
IMMUNOBLOT ANALYSIS

Mixtures of proteins containing LT or LT-B can be separated electrophoretically and the holotoxins or B subunits can be identified by the immunoblot method. As an illustration of the method, 10 μg of LT-BNT was subjected to stacking sodium dodecyl sulfate polyacrylamide gel electrophoresis by the method of Laemmli [Nature 227: 680–685 (1970)], using a 5% spacer and a 13% resolving gel.

Following electrophoresis, the gel was soaked for 45 minutes at 4° C. in an electroelution buffer containing 25 mM Tris-HCl, pH 8.3, with 192 mM glycine and 20% methanol. The proteins were transferred from the swollen gel to nitrocellulose paper (BA 85, Schleicher and Schuell) by electrophoresis in a Hoeffer Scientific Transphor electrotransfer unit, using the maximum amperage for two hours at 4° C.

To detect the LT-BNT, the nitrocellulose sheet was developed two ways. One section of the sheet was stained with Amido Black to reveal all transferred proteins. The remaining section of the sheet was soaked overnight at 4° C. in PBS buffer containing 0.1% sodium azide and 1% ovabumin (PBS-Az-O) to block the remaining protein binding sites. The blocked nitrocellulose was then washed three times, for 10 minutes each, with PBS-T. Lanes containing LT-BNT were exposed for 2 hours at room temperature, either to affinity chromatographically purified goat anti-LT-BNT antiserum (Section 6.12.2) or to serum depleted of LT-BNT-binding antibodies by affinity chromatography. These serum preparations had been diluted 1–500 and 1–10$^6$, respectively, with PBS-Az-O prior to use.

After the exposure to the sera was complete, the sheets were washed three times for 10 minutes each with PBS-T and then incubated for 1 hour at room temperature with horseradish peroxidase-linked anti-goat immunoglobulin, diluted 1,000-fold with PBS containing 1% ovalbumin. The sheets were again washed for three 10-minute periods with PBS-T, after which they were incubated with substrate (0.3 mg 3,3'-diaminobenzidine-HCl/ml of 50 mM Tris-HCl, pH 7.6, with 0.005% $H_2O_2$) for 30 minutes at room temperature. Reaction was stopped by immersing the sheets in water and air drying them, and the locations of LT-BNT were indicated by brown bands.

6.14.3. LATEX BEAD AGGLUTINATION

Latex beads coated with either antigen or antibody can be used to detect the corresponding specific antibody or antigen. To carry out the test to detect antibodies to LT-BNT, 0.8μ latex beads (Difco Laboratories, Detroit Mich.) were added to an equal volume of 1 μg/ml purified LT-BNT in 0.1M glycine buffer, pH 8.2, with 0.15M NaCl. The suspension was incubated for two hours at 37° C. with gentle shaking, to ensure effective bead coating.

After the incubation, the beads were washed by gentle centrifugation for 12 minutes at 1000×g. The supernatant fluid was replaced with PBS containing 0.1% bovine serum albumin, and Bromphenol Blue and sodium azide were added to the suspension, to final concentrations of 0.04 and 0.1%, respectively. To carry out the agglutination assay for anti-LT-BNT antibodies, 5 μl of the sensitized bead suspension was mixed with 15 μl of PBS control buffer or a test sample diluted with PBS. Agglutination, which was read immediately after mixing, was defined as a change from a milky (control) suspension to a particulate suspension with a cleared background.

The agglutination assay was also applied to the detection of LT-BNT in samples by sensitizing the beads in an equal volume of the glycine buffer containing 0.25 mg/ml affinity purified goat antiserum or 0.1 mg/ml murine monoclonal antibodies to LT-BNT.

6.15. DEPOSIT OF MICROORGANISM

The LT-BNT-producing *E. coli* strain harboring plasmid PJC217 has been deposited with the Agricultural Research Culture Collection (NRRL), Peoria, Ill. and has been assigned the accession number NRRL B-15757. A culture of the deposited microorganism will be made available to the public upon the grant of a patent based upon the present application. The inventin described and claimed herein is not to be limited in scope by the strain of microorganism deposited, since the deposited embodiment is intended as a single illustration of the invention. Any equivalent microorganisms that produce functionally equivalent enterotoxin subunits are within the scope of the invention.

We claim:

1. A conjugate of a PRP polysaccharide fragment, having reducing terminal groups derived from the capsular polysaccharide of *Haemophilus influenzae* type b by selective acidic hydrolysis of a portion of the ribosyl ribitol linkages therein, and a bacterial binding subunit, which binding subunit is a non-toxic polypeptide, having one or more immunoreactive and antigenic determinants of an LT-B subunit of the heat-labile enterotoxin of *Escherichia coli* (LT-BNT).

2. The conjugate of claim 1, wherein the nontoxic polypeptide is produced by an *Escherichia coli* bacterium that has been deposited with the NRRL and assigned accession No. B-15757, or by a mutant, recombinant, or genetically engineered equivalent derivative thereof.

3. The conjugate of claim 1, prepared by the reductive amination of the PRP fragment and protein.

4. The conjugate of claim 1, prepared by reductive amination in the presence of cyanoborohydride anions.

5. The conjugate of claim 1, wherein said PRP fragment elutes from a column of Bio-Gel P-10 at a Ve/Vo ratio of $\leq 1.08$.

6. The conjugate of claim 1, wherein said PRP fragment elutes from a column of Bio-Gel P-10 at a Ve/Vo ratio of 1.09–1.38.

7. The conjugate of claim 1 wherein said PRP fragment elutes from a column of Bio-Gel P-10 at a Ve/Vo ratio of 1.39–1.99.

8. The conjugate of claim 1, wherein said PRP fragment elutes from a column of Bio-Gel P-10 at a Ve/Vo ratio of 2.0–2.4.

9. A vaccine that elicits effective levels of anti-PRP antibody formations in young warm-blooded mammals comprising an immunogenic amount of the conjugate of claim 5 and a pharmaceutically acceptable carrier.

10. A vaccine that elicits effective levels of anti-PRP antibody formations in young warm-blooded mammals comprising an immunogenic amount of the conjugate of claim 6 and a pharmaceutically acceptable carrier.

* * * * *